United States Patent [19]

Fukuda et al.

[11] Patent Number: 5,665,233

[45] Date of Patent: Sep. 9, 1997

[54] FILTER APPARATUS FOR SELECTIVELY REMOVING LEUKOCYTES

[75] Inventors: Tatsuya Fukuda; Takao Nishimura; Naokuni Yamawaki, all of Oita, Japan

[73] Assignee: Asahi Medical Co., Ltd., Tokyo, Japan

[21] Appl. No.: 531,700

[22] Filed: Sep. 21, 1995

Related U.S. Application Data

[62] Division of Ser. No. 353,335, Dec. 5, 1994, Pat. No. 5,478,470, which is a continuation of Ser. No. 946,454, Nov. 13, 1992, abandoned.

[30] Foreign Application Priority Data

| Aug. 22, 1991 | [JP] | Japan | ................................ 3-233702 |
| Jul. 9, 1992 | [JP] | Japan | ................................ 4-204265 |

[51] Int. Cl.⁶ .......................... B01D 29/00; B01D 29/05
[52] U.S. Cl. .................. 210/483; 210/489; 210/496; 210/506
[58] Field of Search ........................ 210/500.1, 483, 210/500.21, 496, 500.22, 503, 505, 506, 507, 508, 510.1, 323.1, 489, 435, 446

[56] References Cited

U.S. PATENT DOCUMENTS

| 4,246,107 | 1/1981 | Takenaka et al. | ....................... 210/806 |
| 4,880,548 | 11/1989 | Pall et al. | ....................... 210/767 |
| 4,923,620 | 5/1990 | Pall | ....................... 210/767 |
| 4,925,572 | 5/1990 | Pall | ....................... 210/767 |
| 4,936,998 | 6/1990 | Nishimura et al. | ....................... 210/496 |
| 5,298,165 | 3/1994 | Oka et al. | ....................... 210/645 |
| 5,344,561 | 9/1994 | Pall et al. | ....................... 210/508 |

FOREIGN PATENT DOCUMENTS

| 0370584 | 5/1990 | European Pat. Off. . |
| 0397403 | 11/1990 | European Pat. Off. . |
| 0406485 | 1/1991 | European Pat. Off. . |
| 58-206527 | 12/1983 | Japan . |
| 60-193468 | 10/1985 | Japan . |
| 63-26089 | 5/1988 | Japan . |
| 1224324 | 9/1989 | Japan . |
| 0347131 | 2/1991 | Japan . |
| 3173825 | 7/1991 | Japan . |
| 8705812 | 10/1987 | WIPO . |

*Primary Examiner*—John Kim
*Attorney, Agent, or Firm*—Birch, Stewart, Kolasch & Birch, LLP

[57] ABSTRACT

Disclosed is a filter material for selectively removing leukocytes from a leukocyte-containing suspension, which comprises a porous element having an average pore diameter of 1 to 25 μm and a total pore volume of 0.40 to 0.95 ml/ml of the porous element, and wherein the sum of respective pore volumes of pores of the porous element which have a pore diameter of 1 to 30 μm is 90% or more, based on said total pore volume. Also disclosed is a filter apparatus for selectively removing leukocyte from a leukocyte-containing suspension which is packed with the above-mentioned filter material. By virtue of the filter material, the filter apparatus not only can remove leukocytes from a leukocyte-containing suspension at a leukocyte removal efficiency as excellent as $10^{-4}$ or less in terms of a leukocyte residual ratio without suffering from a pressure loss increase, but also can be rendered compact.

10 Claims, No Drawings

FILTER APPARATUS FOR SELECTIVELY REMOVING LEUKOCYTES

This application is a divisional of application Ser. No. 08/353,335, filed on Dec. 5, 1994, now U.S. Pat. No. 5,478,470, which is a continuation of application Ser. No. 07/946,454 filed on Nov. 13, 1992 (now abandoned) the entire contents of which are hereby incorporated by reference.

TECHNICAL FIELD

The present invention relates to a filter material comprising a porous element and to a filter apparatus for selectively removing leukocytes which is packed with the filter material. More particularly, the present invention is concerned with a filter material for selectively removing leukocytes, by which leukocytes can be efficiently removed from a leukocyte-containing suspension, such as whole blood, a red cell product or a platelet product. Also, it is concerned with a filter apparatus for selectively removing leukocytes which is packed with the above-mentioned filter material, which is compact, and in which a pressure loss increase can be minimized.

BACKGROUND ART

In recent years, in accordance with the progress of immunology and science of transfusion, a blood component transfusion, in which only a blood component required to treat a particular disease is transfused, is now increasingly carried out in place of the conventional whole blood transfusion. The blood component transfusion is a therapy which is desirable because the burden on a patient receiving transfusion can be alleviated, and because it ensures a high treatment efficacy. Various types of blood products, such as concentrated red cells (CRC), concentrated platelet cells (PC) and platelet-poor plasma (PPP), are employed in the blood component transfusion, and are prepared by subjecting donated whole blood to centrifugation. It has become apparent, however, that blood products obtained by centrifugation separation contain leukocytes in high concentration, and that side effects of transfusion are caused by the contained leukocytes. Side effects of transfusion include not only relatively mild side effects, such as headache, nausea, chilliness and nonhemolytic feverish reaction, but also serious side effects. Particularly with respect to the latter, when a transfusion recipient has an immunopathy, transfusion is likely to cause serious side effects, such as graft versus host (GVH) reaction, in which transfused leukocytes attack the skin and internal organs of the transfusion recipient, infections by viruses present in the leukocytes, e.g., cytomegalovirus infection, and allosensitization. The above-mentioned side effects of transfusion reactions can be effectively prevented by capturing and removing the leukocytes contained in the blood products.

Generally, blood products for use in transfusion, such as whole blood and a red cell product, contain $10^7$ leukocytes per ml. It is recognized that the number of leukocytes injected into a recipient at one transfusion must be limited to about 100,000,000 or less for avoiding relatively mild side effects, such as headache, nausea, chilliness and feverish reaction. To meet this requirement, leukocytes must be removed from a blood product to a level of $10^{-1}$ to $10^{-2}$ or less in terms of a leukocyte residual ratio. For preventing allosensitization and vital infections, however, leukocytes must be removed from a blood product to a level of $10^{-4}$ to $10^{-6}$ or less, in terms of a leukocyte residual ratio.

The methods for removing leukocytes from a blood product can generally be classified into two methods. One is a method in which leukocytes are separated by a centrifugation, taking advantage of a difference in specific gravity. The other is a filtering method in which leukocytes are removed by filtration, using a filter comprising as a filter material a fibrous porous medium, such as a non-woven fabric, or a porous article having a three-dimensional network of continuous pores. In particular, the filtering method is widely employed due to the advantages that leukocytes can be removed with high efficiency, handling is easy and cost can be reduced.

In recent years, intensive studies have been made to develop filter apparatus for removing leukocytes. Especially, it is strongly desired in the art to develop a filter apparatus which not only has the ability to effectively remove leukocytes but also is free from a pressure loss increase due to blood cell clogging, so that blood filtration can be continuously performed without interruption.

It is known that removal of leukocytes is mainly attained by adhesion. Accordingly, the difference in leukocyte removal efficiency between filter materials which are comprised of the same material and have similar surfaces, is considered to be dependent on the degree of collision frequency between the filter materials and leukocytes. For improving the leukocyte removal efficiency, it is desired that the surface of a filter material, to which leukocytes will adhere, be larger so that the collision frequency is increased between the filter material and leukocytes. Actually, an increase of the surface area of a filter material is generally accomplished by the employment of extremely fine fibers having an average fiber diameter of about 1 to 3 μm, when the filter material is comprised of a fibrous, porous medium, such as a non-woven fabric (see Japanese Patent Application Laid-Open Specification No. 60-193468/1985). On the other hand, when the filter material is comprised of a porous article having a uniform average pore diameter, the increase of the surface area is generally accomplished by the employment of porous articles having an average pore diameter as small as from 5 to 20 μm (see Japanese Patent Application Published Specification No. 63-26089/1988 and Japanese Patent Application Laid-Open Specification No. 3-173825/1991).

When a filter material comprised of a fibrous, porous medium, such as a non-woven fabric is used, for improving the leukocyte removal efficiency per volume of a filter apparatus for removing leukocytes, it has generally been required either to increase the packing density of the filter material so as to substantially increase the amount of the filter material, or to employ a fibrous, porous medium having a smaller fiber diameter. The upper limit of the packing density of the filter material is about 0.4 g/cm³. Beyond this upper limit, packing of, for example, a non-woven fabric, into a filter container becomes difficult due to the resiliency of the non-woven fabric. If a hot compression is performed to avoid the resiliency, the non-woven fabric is collapsed into a film form, which is no longer useful as a filter material. Therefore, for improving the leukocyte removal efficiency, it has been necessary to adopt either a method in which the amount of the filter material is increased while keeping the packing density thereof at 0.4 g/cm³ or less, or a method in which a filter material comprising fibers having a smaller average fiber diameter is employed. When a porous article having a uniform average pore diameter is used as a filter material, it has been necessary to keep the pore diameter as small as possible, for improving the leukocyte removal efficiency. In any of these measures for improving the leukocyte removal efficiency, however, there has been a problem that the improvement of the leukocyte removal efficiency is inevitably accompanied by an increase of a pressure loss in the filter material during the passage of a blood product, so that the filtration rate decreases significantly before completion of the filtration of a predetermined amount of the blood product.

With respect to a spongy structure as a porous article, Japanese Patent Application Laid-Open Specification No. 1-224324/1989 discloses,a structure having a bubble point of from 0.08 to 0.3 kg/cm$^2$, which is described as being a leukocyte separator free from the danger of clogging with leukocytes. The present inventors have examined the leukocyte separator. As a result, they have found that the ability of the separator to remove the leukocytes contained in a blood product is only about $10^{-2}$ to $10^{-3}$ in terms of a leukocyte residual ratio. When a porous article having an extremely small average pore diameter is employed in order to attain a leukocyte residual ratio of $10^{-4}$, it has had drawbacks. That is, a porous article having an optimal average pore diameter can exhibit the same degree of leukocyte removal efficiency as attained by a non-woven fabric, even though the thickness of the porous article is a small fraction of that of the non-woven fabric, so that an advantageous means can be provided for attaining miniaturization, however, a porous article capable of exhibiting a leukocyte residual ratio of $10^{-4}$ disadvantageously suffers from a pressure loss increase due to clogging with leukocytes. This clogging causes the blood filtration rate to be extremely low, as in the use of a non-woven fabric having an extremely small diameter.

EP 0406485 A1 discloses a filter apparatus for removing leukocytes which is allegedly capable of solving the above-mentioned drawbacks. The filter apparatus is packed with a porous article as a filter material which has an average pore diameter gradient such that the average pore diameter is decreased in a flow direction in which blood is adapted to be flowed from an upstream end portion to a downstream end portion of the porous article, in order to avoid a blood cell clogging of the upstream end surface of the porous article. However, although some drawbacks, such as pressure loss increase and filtration time prolongation due to blood cell clogging, can be overcome by the use of the leukocyte-removing filter apparatus disclosed in EP 0406485 A1, this apparatus cannot satisfactorily prevent leakage of lymphocytes which have a relatively low adherence and a relatively small size among leukocytes, so that the leukocyte residual ratio attained by the apparatus is disadvantageously as high as about $10^{-1}$ to $10^{-2}$.

As described above, no leukocyte-removing filter apparatus has heretofore been proposed which exhibits a leukocyte removal efficiency as excellent as $10^{-4}$ or less in terms of a leukocyte residual ratio, and which ensures smooth blood filtration.

Miniaturization of a filter apparatus is an important theme to be attained regarding a leukocyte-removing filter apparatus, like the improvement of a leukocyte removal efficiency and the attainment of a smooth blood filtration. Usually, after completion of the filtration operation to remove leukocytes, the blood product remaining inside the filter apparatus is discarded together with the filter apparatus. Therefore, to minimize the waste of the blood product, a filter apparatus having a small hold-up volume is desired. The terminology "hold-up volume" used herein means the volume of the whole space inside a leukocytes removing filter apparatus. Generally, it is desired that the proportion of the blood product discarded with a filter apparatus be limited to a level as low as 10–15% or less. For meeting this, it is desired that the filter apparatus be of such a small size as to have a hold-up volume as small as 35 ml or less per unit of whole blood or a red cell product or as small as 20 ml or less per 5 units of a platelet product.

In addition, there has been a problem that an increase in the surface area of a filter material and in the hold-up volume of a leukocyte-removing filter apparatus is likely to cause the recovery of desired non-leukocyte blood components, such as red cells and platelets, to be poor. In particular, platelets have high adherence, and hence, the employment of a filter material having too large a surface area causes the recovery of platelets to be extremely poor.

DISCLOSURE OF THE INVENTION

In the above situations, the present inventors have made extensive and intensive studies with a view toward developing a filter material for selectively removing leukocytes, which is less likely to suffer from a clogging with blood cells and exhibits a leukocyte removal efficiency as excellent as $10^{-4}$ or less in terms of a leukocyte residual ratio. As a result, it has been found that a filter material for removing leukocytes, which comprises a porous element having an average pore diameter and a total pore volume in specific ranges, wherein the sum of respective pore volumes of pores of the porous element which have a pore diameter of 1 to 30 μm is 90% or more, based on the total pore volume, is not only less likely to be clogged with blood cells, but also does not suffer from a lowering of the filtration rate of a leukocyte-containing suspension, and exhibits an excellent leukocyte removal efficiency. Moreover, it has been found that these advantages are remarkably promoted by the employment of a porous element having a specific total pore surface area, wherein the proportion of the sum of respective pore surface areas of pores of the porous element which have a pore diameter of from 1 to 30 μm or from 1 to 10 μm to the total pore surface area is not less than a certain value. The present invention has been completed on the basis of the above findings.

It is an object of the present invention to provide a novel filter material for selectively removing leukocytes, which is improved in the prevention of leukocyte leakage and the prevention of clogging with blood cells, as compared to the conventional leukocyte-removing filter materials. More particularly, this object is to provide a novel filter material for selectively removing leukocytes, which is improved in the leukocyte removal efficiency per volume so as to exhibit a leukocyte removal efficiency as excellent as $10^{-4}$ or less in terms of a leukocyte residual ratio, and which can be used in blood filtration without suffering from a lowering of a filtration rate, i.e., without suffering from a clogging with blood cells and an increase of pressure loss.

It is another object of the present invention to provide a filter apparatus for selectively removing leukocytes, which not only does not suffer from a pressure loss increase, but also is of a small size and can be used to filter a leukocyte-containing suspension at a leukocyte removal efficiency as excellent as $10^{-4}$ or less in terms of a residual ratio of leukocytes present in the resultant suspension filtrate.

The foregoing and other objects, features and advantages of the present invention will be apparent from the following detailed description and appended claims.

Essentially, according to the present invention, there is provided a filter material for selectively removing leukocytes from a leukocyte-containing suspension, which comprises a porous element having an average pore diameter of 1 to 25 μm and a total pore volume of 0.40 to 0.95 ml/ml of the porous element, wherein the sum of respective pore volumes of pores of the porous element which have a pore diameter of 1 to 30 μm is 90% or more, based on the total pore volume.

With respect to the porous element of the filter material for selectively removing leukocytes according to the present invention, preferred conditions are set forth below.

(1) the porous element has a total pore surface area of 0.50 to 5.70 m$^2$/ml of the porous element, with the proviso that the sum of respective pore surface areas of pores of the porous element which have a pore diameter of 1 to 30 μm is 60% or more, based on the total pore surface area;

(2) the sum of respective pore surface areas of pores of the porous element which have a pore diameter of 1 to 10 μm is 50% or more, based on the total pore surface area;

(3) the sum of respective pore surface areas of pores of the porous element which have a pore diameter of less than 1 μm is 38% or less, based on the total pore surface area, and the sum of respective pore volumes of pores of the porous element which have a pore diameter of more than 30 μm is 6% or less, based on the total pore volume;

(4) the porous element has a critical wetting surface tension of at least 65 dyn/cm;

(5) the porous element has, in a surface portion thereof, a basic functional group at a density of $10^{-6}$ to 3 meq/m$^2$;

(6) the porous element has, in a surface portion thereof, an acidic functional group at a density of $10^{-4}$ to 5 meq/m$^2$;

(7) the porous element is a fibrous, porous medium selected from the group consisting of a knit fabric, a woven fabric and a non-woven fabric, each comprising fibers having an average fiber diameter of 0.3 to 3.0 μm; or (8) the porous element is a porous article selected from the group consisting of a porous membrane and a spongy structure having a three-dimensional network of continuous pores;

(9) particularly when the leukocyte-containing suspension to be subjected to filtration is a leukocyte-containing red cell product;

(9-1) the porous element has an average pore diameter of 3 to 25 μm and a total pore volume of 0.40 to 0.95 ml/ml of the porous element, with the proviso that the sum of respective pore volumes of pores of the porous element which have a pore diameter of 2 to 30 μm is 85% or more, based on the total pore volume;

(9-2) the porous element has a total pore surface area of 0.50 to 5.70 m$^2$/ml, with the proviso that the sum of respective pore surface areas of pores of the porous element which have a pore diameter of 2 to 30 μm is 50% or more, based on the total pore surface area;

(9-3) the sum of respective pore surface areas of pores of the porous element which have a pore diameter of 2 to 10 μm is 35% or more, based on the total pore surface area;

(9-4) the sum of respective pore volumes of pores of the porous element which have a pore diameter of less than 2 μm is 8% or less, based on the total pore volume, and the sum of respective pore surface areas of pores of the porous element which have a pore diameter of less than 2 μm is less than 40%, based on the total pore surface area;

(9-5) the porous element has a critical wetting surface tension of 65 to 90 dyn/cm;

(9-6) the porous element has, in a surface portion thereof, a basic functional group at a density of $10^{-4}$ to 3 meq/m$^2$; or (9-7) the porous element has, in a surface portion thereof, an acidic functional group at a density of $5\times10^{-2}$ to 5 meq/m$^2$; and/or (9-8) the porous element is a fibrous, porous medium selected from the group consisting of a knit fabric, a woven fabric and a non-woven fabric, each comprising fibers having an average fiber diameter of 0.3 to 3.0 μm; or (9-9) the porous element is a porous article selected from the group consisting of a porous membrane and a spongy structure having a three-dimensional network of continuous pores;

(10) particularly when the leukocyte-containing suspension to be subjected to filtration is a leukocyte-containing platelet product;

(10-1) the porous element has an average pore diameter of 1 to 15 μm, with the proviso that the sum of respective pore volumes of pores of the porous element which have a pore diameter of 1 to 25 μm is 85% or more, based on the total pore volume;

(10-2) the porous element has a total pore surface area of 0.50 to 5.70 m$^2$/ml of the porous element, with the proviso that the sum of respective pore surface areas of pores of the porous element which have a pore diameter of 1 to 25 μm is 58% or more, based on the total pore surface area;

(10-3) the sum of respective pore surface areas of pores of the porous element which have a pore diameter of 1 to 10 μm is 55% or more, based on the total pore surface area;

(10-4) the sum of respective pore volumes of the porous element which have a pore diameter of more than 25 μm is 10% or less, based on the total pore volume, and the sum of respective pore surface areas of pores of the porous element which have a pore diameter of more than 25 μm is 4% or less, based on the total pore surface area;

(10-5) the porous element has a critical wetting surface tension of at least 85 dyn/cm;

(10-6) the porous element has, in a surface portion thereof, a basic functional group at a density of $10^{-6}$ to $10^{-1}$ meq/m$^2$; or (10-7) the porous element has, in a surface portion thereof, an acidic functional group at a density of $10^{-4}$ to 1 meq/m$^2$; and/or (10-8) the porous element is a fibrous, porous medium selected from the group consisting of a knit fabric, a woven fabric and a non-woven fabric, each comprising fibers having an average fiber diameter of 0.3 to 3.0 μm; or (10-9) the porous element is a porous article selected from the group consisting of a porous membrane and a spongy structure having a three-dimensional network of continuous pores.

In the present invention, with respect to the porous element, the average pore diameter, the total pore volume, the respective pore volumes of pores having specific pore diameters, the total pore surface area and the respective pore surface areas of pores having specific pore diameters, are measured by mercury porosimetry (using Poresizer® 9320 of Shimazu Corporation, Japan). The terminology "average pore diameter" used herein means a diameter falling on a point where the amount of mercury penetrated into pores under a pressure is 50%, provided that the amount of mercury penetrated into pores under the pressure is regarded as 0% when no trace of mercury is penetrated into the pores of a porous element, and that the amount of mercury penetrated into pores under the pressure is regarded as 100% when all the pores of the porous element are filled with mercury. The pore volume of a porous element of the present invention is the product of the pore volume (cc/g or ml/g) of the element determined by mercury porosimetry, multiplied by the bulk density (g/cm$^3$ or g/ml) of the element. The pore surface area of the porous element is the product of the specific surface area m$^2$/g) of the element determined by the mercury porosimetry, multiplied by the bulk density of the element. The above measurement by mercury porosimetry is made under substantially the same condition as employed in actually packing the porous element in a filter apparatus for selectively removing leukocytes.

The average pore diameter of the porous element of the filter material ofthe present invention, can be obtained by a method which comprises first cutting the porous element in a direction perpendicular to a flow direction in which a leukocyte-containing suspension is adapted to be flowed to thereby obtain a cross-section, secondly identifying pores having substantially the same size which are most abundant among various pores distributed over the cross-section, and obtaining the pore size of the identified most abundant pores in terms of the diameter of a circle having the same area as the cross-sectional area of the identified pores. Illustratively stated, the pores distributed over an arbitrary cross-section of the porous element may have various morphologies with various sizes. With respect to individual pores, respective cross-sectional areas are obtained in terms of respective diameters of circles having the same areas as the respective cross-sectional areas of the pores. When the number of the pores (ordinate) is plotted against the diameter (abscissa) of the corresponding circle, a nearly normal distribution curve is obtained. The average pore diameter used herein is defined as the diameter falling on the peak of the normal dfstribution curve. As is apparent from the above, the average pore diameter represents an average diameter of the circles corresponding to the pores distributed over every arbitrary cross-section, and it is necessary in the present invention that the average pore diameter on any of the cross-sections be in the range of from 1 to 25 μm.

With respect to the measurement by mercury porosimetry under pressure using a mercury porosimeter, the pressure is generally in the range of from 1 to 2650 psi.

The density of a basic functional group or an acidic functional group which is optionally present in a surface portion of the porous element of the present invention, can be measured by conventional techniques, such as infrared absorption spectroscopy, nuclear magnetic resonance spectroscopy and elemental analysis. The measurement of the density can also be conducted by easier methods, such as titration and dye adsorption methods.

The porous element of the filter material according to the present invention is not particularly limited as long as it has pores adapted for blood filtration and has specific characteristics recited as being essential in the present invention, and the morphology of the porous element is not critical. In particular, representative examples of such porous elements include a porous article selected from the group consisting of a porous membrane and a spongy structure having a three-dimensional network of continuous pores. Further, representative examples of such porous elements include a fibrous, porous medium selected from the group consisting of a cottonlike fiber mass, a knit fabric, a woven fabric and a non-woven fabric. A porous article is most preferred as the porous element.

Materials for the porous element of the filter material according to the present invention are not particularly limited as long as they are not likely to damage blood cells, and various types of materials can be employed, including organic polymers, inorganic polymers and metals. Of these, organic polymers are preferred because of excellent workability, e.g., good cuttability. Examples of such organic polymers include a polyurethane, polyacrylonitrile, polyvinyl alcohol, polyvinyl acetal, polyester, polyamide, polystyrene, polysulfone, cellulose, cellulose acetate, polyethylene, polypropylene, polyvinyl fluoride, polyvinylidene fluoride, polytrifluorochloroethylene, polyvinylidene fluoride-tetrafluoroethylene copolymer, polyethersulfone, poly(meth)acrylate, butadieneacrylonitrile copolymer, polyether-polyamide block copolymer and ethylene-vinyl alcohol copolymer. The materials for the porous element of the present invention are not limited to the above examples.

The porous element of the filter material for selectively removing leukocytes according to the present invention can be produced by conventional techniques. A porous article as an example of such porous elements can be produced by any one of the decomposition-foaming methods (such as the atmospheric foaming method, pressure foaming method, extrusion foaming method or injection foaming method), the solvent evaporation method, the gas incorporation method, the chemical reaction method, the dissolutionout method and the firing method. The produced porous article is preferably subjected to secondary processing, such as hot press compression and swelling with an appropriate liquid, so that the article has a specific pore diameter distribution which is requisite to the present invention. On the other hand, a fibrous, porous medium as another example of the above-mentioned porous elements can be produced by conventional techniques, such as the melt blow method and the flash spinning method. The produced fibrous, porous medium is preferably subjected to secondary processing, such as press compression, thermal shrinkage and treatment with an appropriate liquid, so that the medium has a specific pore diameter distribution which is requisite to the present invention.

The terminology "leukocyte-containing suspension" used herein means a liquid in which leukocytes are suspended. Examples of leukocyte-containing suspensions include whole blood; red cell products, such as concentrated red cells, washed red cells, leukocyte-removed red cells, thawed red cell concentrate and thawed red cell suspension; plasma products, such as platelet-poor plasma, platelet-enriched plasma, fresh lyophilized plasma, fresh liquid plasma and cryoprecipitate; and other leukocyte-containing blood products, such as concentrated platelet cells, buffy coat and buffy coat-removed blood. The leukocyte-containing suspension to be treated in the present invention is not limited to the above examples.

The blood cell components of a blood product include red cells, platelets, and leukocytes as a generic term for granulocytes, monocytes and lymphocytes. The sizes of a platelet, a red cell, a lymphocyte, a granulocyte and a monocyte are, respectively, in the ranges of about from 2 to 4 μm, about from 4 to 9 μm, about from 6 to 12 μm, about from 10 to 15 μm, and about from 13 to 20 μm. The individual blood cell components more or less exhibit a metaboly as typically possessed by red cells. The adherence to a polymer material is believed to be in the order of monocyte>granulocyte>platelet>lymphocyte>red cell.

The present inventors noticed the importance of the size and adherence of each blood cell component and made extensive and intensive studies. As a result, they have found that the pore diameter at which leukocytes can be effectively removed is in the range of from 1 to 30 μm. Based on this finding, the filter material for selectively removing leukocytes according to the present invention has been developed. Illustratively stated, it has been found by the inventors that monocytes and granulocytes, as member of the leukocyte family, can easily be removed even at pore diameters at which their contact frequency with a polymer material is relatively small, i.e. at pore diameters of up to about 30 μm, because they have relatively large size and high adherence, while the effective minimum pore diameter for removing lymphocytes as another member of the leukocyte family is about 1 μm when their metaboly is taken into account, because the lymphocytes have a smaller and a lower adherence than those of monocytes and granulocytes, so that for removal of lymphocytes, sifting-removal by particle diameter is important in addition to the removal by adherence.

Therefore, for effective removal of leukocytes from a blood product, attention should be drawn to pores having a pore diameter of from 1 to 30 μm. The filter material for selectively removing leukocytes according to the present invention is characterized by having an average pore diameter of 1 to 25 μm, wherein the ratio of the sum of respective pore volumes of pores having a pore diameter of 1 to 30 μm, which is effective for removing leukocytes, is high relative to the total pore volume.

Illustratively stated, with respect to the porous element of the filter material of the present invention for selectively removing leukocytes, it is requisite. that the total pore volume of the porous element be in the range of from 0.40 to 0.95 ml/ml of the porous element and that, in the porous element, the sum of respective pore volumes of pores having a pore diameter of 1 to 30 μm be 90% or more, based on the total pore volume.

Further, with respect to the porous element of the filter material of the present invention for selectively removing leukocytes, it is preferred that the porous element have a total pore surface area of 0.50 to 5.70 m²/ml of the porous element and that, in the porous element, the sum of respective pore surface areas of pores having a pore diameter of 1 to 30 μm be 60% or more, based on the total pore surface area. In addition to the pore volume, the pore surface area is also an important physical property of the filter material for selectively removing leukocytes. Specifically, a filter material for selectively removing leukocytes, in which, with respect to pores having a pore diameter of 1 to 30 μm and thus being effective for the removal of leukocytes, not only the sum of respective pore surface areas thereof but also the sum of respective pore volumes thereof are large, exhibits an excellent leukocyte removal efficiency.

Furthermore, for preventing a leakage of leukocytes, it is preferred that the porous element have a narrow pore diameter distribution. The coefficient of variation obtained by dividing the standard deviation value of the pore diameter distribution by an average pore diameter is preferably 10% or less, more preferably 5% or less.

As mentioned above, in the porous element of the filter material of the present invention for selectively removing leukocytes, the sum of respective pore volumes of pores having a pore diameter of 1 to 30 μm is 90% or more, based on the total pore volume. The sum of respective pore volumes of pores having a pore diameter of larger than 30 μm is preferably 6% or less, based on the total pore volume. The total pore volume is preferably 0.50 to 0.95 ml/ml of the porous element, more preferably 0.60 to 0.95 ml/ml of the porous element. In the porous element, the sum of respective pore volumes of pores having a pore diameter of 1 to 30 μm is preferably 95% or more, more preferably 98% or more, based on the total pore volume. The sum of respective pore volumes of pores having a pore diameter of larger than 30 μm is more preferably 4% or less, most preferably 2% or less, based on the total pore volume. When the total pore volume is less than 0.40 ml/ml of the porous element, the total pore volume is insufficient for blood to pass through the pores, thus causing the porous element to be clogged with blood cells. On the other hand, when the total pore volume is more than 0.95 ml/ml of the porous element, the strength of the porous element is lowered, so that the porous element can no longer function as a filtering material. In the case of a porous element in which the sum of respective pore volumes of pores having a pore diameter of 1 to 30 μm is less than 90%, based on the total pore volume, the amount of pores effective for the removal of leukocytes is small, thereby causing leukocytes to leak out or causing the porous element to be clogged with blood cells. When the sum of respective pore volumes of pores having a pore diameter of larger than 30 μm exceeds 6%, based on the total pore volume, the danger of occurrence of a leakage of leukocytes unfavorably increases, thus rendering it impossible to effectively remove leukocytes.

Further, it is preferred that the porous element of the filter material of the present invention for selectively removing leukocytes have a total pore surface area of 0.50 to 5.70 m²/ml of the porous element and that, in the porous element, the sum of respective pore surface areas of pores having a pore diameter of 1 to 30 μm be 60% or more, based on the total pore surface area, the sum of respective pore surface areas of pores having a pore diameter of 1 to 10 μm be 50% or more, and the sum of respective pore surface areas of pores having a pore diameter of less than 1 μm be 38% or less, based on the total pore surface area. The total pore surface area of the porous element is more preferably from 0.70 to 5.70 m²/ml of the porous element, further more preferably from 0.80 to 5.70 m²/ml of the porous element, most preferably from 0.90 to 5.70 m²/ml of the porous element. In the porous element, the sum of respective pore surface areas of pores having a pore diameter of 1 to 30 μm is more preferably 65% or more, most preferably 70% or more, based on the total pore surface area. The sum of respective pore surface areas of pores having a pore diameter of 1 to 10 μm is more preferably 55% or more, most preferably 60% or more, based on the total pore surface area. Further, the sum of respective pore surface areas of pores having a pore diameter of less than 1 μm is more preferably 30% or less, most preferably 28% or less, based on the total pore surface area. When the total pore surface area is less than 0.50 m²/ml of the porous element, the total pore surface area is insufficient for the effective adhesion of leukocytes, so that a leakage of leukocytes would occur. When the total pore surface area is more than 5.70 m²/ml of the porous element/the time required for the treatment of blood is prolonged, and not only leukocytes but also red cells and platelets are likely to be removed, so that the pressure loss is unfavorably increased due to a clogging of the porous element. When the sum of respective pore surface areas of pores having a pore diameter of 1 to 30 μm is less than 60%, based on the total pore surface area, the sum of respective pore surface areas of pores effective for the removal of leukocytes is small, so that a leakage of leukocytes or a clogging of the porous element is likely to occur. When the sum of respective pore surface areas of pores having a pore diameter of 1 to 10 μm is less than 50%, based on the total pore surface area, a leakage of lymphocyteS or a clogging of the porous element is likely to occur. Since pores having a pore diameter of less than 1 μm is too fine for blood cells to pass through, when the sum of respective pore surface areas of pores having a pore diameter of less than 1 μm is large, the amount of blood cells which cannot pass through the porous element will increase and accumulate in the porous element. For this reason, when the sum of respective pore surface areas of pores having a pore diameter of less than 1 μm is more than 38%, based on the total pore surface area, the recovery of blood cells other than leukocytes, that is, red cells and platelets, is likely to be lowered. The average pore diameter of the filter material of the present invention for selectively removing leukocytes is in the range of from 1 to 25 μm, preferably from 3 to 20 μm, more preferably from 5 to 18 μm. The average pore diameter of the porous element reflects the pore diameter distribution thereof. When the average pore diameter is less than 1 μm, a clogging of the porous element is caused. When the average pore diameter is more than 25 μm, a leakage of leukocytes would markedly occur.

The critical wetting surface tension (CWST) of the porous element of the filter material of the present invention for selectively removing leukocytes is preferably at least 65 dyn/cm.

The terminology "CWST" used herein is a physical property which is related to the surface properties of the porous element and which is used to determine the wetting properties of the porous element. Specifically, the CWST is a surface property which determines whether or not wetting of the porous element would occur when a liquid is brought into contact with the surface of the porous element and a slight pressure is applied. When the porous element has a CWST value higher than the surface tension of a liquid, wetting of the porous element with the liquid is caused. The present invention relates to a filter material for removing leukocytes from a leukocyte-containing blood product. In practice, in removing leukocytes from a blood product, it is desired that a wetting of the porous element with the blood product occur upon contact therebetween. Therefore, it is preferred that the surface of the porous element to be used in the present invention have a CWST value equal to or higher than the surface tension of a blood product to be subjected to filtration. The surface tensions of blood plasma and red cells have already been measured and known to be 73 dyn/cm and 64.5 dyn/cm, respectively ("Measurement of the surface tensions of blood cells and protein", A. W. Newman et al, New York Academy of Science, 1983, p. 276). A porous element having a surface tension of less than 65 dyn/cm cannot be used as a filter material for blood unless a considerable pressure is applied. Therefore, such a porous element is not preferred. With respect to a porous element having a CWST value of less than 65 dyn/cm, such a porous element can be surface-modified so that the CWST value becomes 65 dyn/cm or more. The surface modification can be conducted by introducing a hydrophilic monomer or polymer to the surface portion of the porous element by the use of a surface modification technique, such as graft polymerization, coating, chemical treatment, plasma treatment or the like. Such a surface-modified porous element having a CWST value of 65 dyn/cm ormore can be advantageously employed in the present invention.

The terminology "CWST" used in the present invention means a value obtained by the following method. That is, aqueous solutions respectively of sodium hydroxide, calcium chloride, sodium nitrate, sodium acetate, acetic acid and ethanol are prepared in varied concentrations with respect to each of the aqueous solution, so that the solutions have surface tensions which are serially different by a value of 2 to 4 dyn/cm. The range of surface tension (dyn/cm) of each of the aqueous solutions obtained is as follows. The aqueous sodium hydroxide solutions have a surface tension of from 94 to 115, the aqueous calcium chloride solutions have a surface tension of from 90 to 94, the aqueous sodium nitrate solutions have a surface tension of from 75 to 87, pure water has a surface tension of 72.4, the aqueous acetic acid solutions have a surface tension of from 38 to 69, and the aqueous ethanol solutions have a surface tension of from 22 to 35 ("Chemistry Handbook, Fundamentals II" ("Kagaku BinRan, Kisohen II") Second Revised Edition, compiled by The Chemical Society of Japan, Maruzen, 1975, p. 164). The thus obtained aqueous solutions, which are serially varied in surface tension by a value of 2 to 4 dyn/cm, are separately placed on the porous element in the form of 10 drops and the drops are allowed to stand for 10 minutes. The aqueous solutions are used in the order of from a low surface tension solution to a high surface tension solution. After the 10 drops have been allowed to stand for 10 minutes, examination is made to determine the number of drops which have been absorbed into the porous element. When 9 or more of the 10 drops have been absorbed into the porous element, it is defined as being wetted with the solution. On the other hand, when the. number of drops which have been absorbed is less than 9 of the 10 drops, it is defined as being non-wetted with the solution. In this way, the testings are successively conducted using the solutions in the order of from a low surface tension liquid to a high surface tension liquid. A wet state and a non-wet state would appear. In this case, an average value of the highest value of surface tension at which a wet state is observed and the lowest value of surface tension at which a non-wet state is observed, is defined as the CWST value of the porous element. For example, when wetting is observed with a liquid having a surface tension of 64 dyn/cm, while non-wetting is observed with a liquid having a surface tension of 66 dyn/cm, the CWST value of the porous element is 65 dyn/cm.

It is preferred that the surface of the porous element of the filter material of the present invention for selectively removing leukocytes be modified by conventional techniques, such as graft polymerization, coating, chemical treatment using an alkali or an acid, and plasma treatment. Especially, graft polymerization and coating have long been known as techniques for modifying the surface of a polymer material. Graft polymerization and coating are excellent surface modification techniques which make it possible to modify the wetting properties and electrical properties of the surface of a polymer material to desired degrees. More particularly, since the interfacial reactions between living cells and the surface of a polymer material are considered to be greatly influenced by the chemical structure of the surface of the polymer material, in designing a filter material for selectively removing leukocytes, attention should be paid to the chemical structure of the surface of the filter material for selectively removing leukocytes as well as the physical structure thereof. Thus, as preferred examples of simple and excellent modification methods for modifying the surface of a porous element to impart a desired chemical structure thereto, there can be mentioned graft polymerization and coating.

The first objective of the surface modification of the porous element of the filter material for selectively removing leUkocytes is to obtain a surface to which leukocytes adhere well, and the second objective is to enable a smooth blood filtration. For attaining these objectives by modifying the surface of the porous element, it is effective to introduce various chemical species, e.g., chemical species having a hydrophilic functional group, such as a hydroxyl group, a polyethylene oxide chain or the like, or chemical species having an electrical charge, into a surface portion of the porous element.

With respect to the porous element of the filter material of the present invention for selectively removing leukocytes, the porous element preferably has, in a surface portion thereof, a basic functional group at a density of $10^{-6}$ to 3 meq/m$^2$, more preferably $10^{-5}$ to 1 meq/m$^2$. Alternatively, the porous element of the filter material preferably has, in a surface portion thereof, an acidic functional group at a density of $10^{-4}$ to 5 meq/m$^2$, more preferably $5 \times 10^{-3}$ to 1 meq/m$^2$. The adherence of leukocytes to a polymer material is affected by the surface properties of the polymer material. Generally, blood cells including leukocytes have a negative electrical charge on their surface. Therefore, polymer materials having a positive charge on the surface thereof are generally known to be effective for the removal of leukocytes (WO/No.05812). Also, a surface having anegative electrical charge is effective for the removal of leukocytes. Since electrostatic repulsive force is produced between cells having a negative charge and an acidic functional group having a negative charge, it is naturally considered that the adherence of cells to the surface of a filter material would be decreased when an acidic functional group is present on the surface of the filtermaterial. However, as mentioned above, the surface having a negative electrical charge is also effective for the removal of leukocytes. As the reason for this, it is presumed that a certain type of protein contained in blood plasma adheres to the surface of the material having an acidic functional group thereon and the adherence of leukocytes is facilitated by the intermediation of the protein. When the density of the basic functional group in the surface portion is less than $10^{-6}$ meq/m$^2$, or when the density of the acidic functional group in the surface portion is less than $10^{-4}$ meq/m$^2$, the electrostatic effect is likely to become poor. When the density of the basic functional group in the surface portion is more than 3 meq/m$^2$, or when the density of the acidic functional group in the surface portion is more than 5 meq/m$^2$, the effect of the functional group would be exerted not only on leukocytes but also on other blood components, namely, red cells and platelets, thus leading to an occurrence of unfavorable phenomena, such as hemolysis.

With respect to a porous element having neither a basic functional group nor an acidic functional group in a surface portion thereof, the introduction of the functional groups into the surface portion of the porous element by surface modification can be performed by a method in which a monomer or a polymer having a basic functional group or an acidic functional group is introduced into the surface of the porous element by graft polymerization or coating so that the porous element has, in a surface portion thereof, the basic functional group at a density of $10^{-6}$ to 3 meq/m$^2$, or that the porous element has, in a surface portion thereof, the acidic functional group at a density of $10^{-4}$ to 5 meq/m$^2$. Such a surface-modified porous element is also included in the scope of the porous element referred to in the present invention.

As basic functional groups usable in the present invention, there can be mentioned, for example, a primary amino group, a secondary amino group, a tertiary amino group, and a quaternary ammonium group, and nitrogen-containing aromatic ring groups, such as a pyridyl group and an imidazoyl group. Examples of monomers having these functional groups include allylamine; (meth)acrylic acid derivatives, such as dimethylaminoethyl (meth)acrylate, diethylaminoethyl (meth)acrylate, dimethylaminopropyl (meth)acrylate, and 3-dimethylamino-2-hydroxypropyl (meth)acrylate; and styrene derivatives, such as p-dimethylaminomethylstyrene and p-diethylaminoethylstyrene; and vinyl derivatives of nitrogen-containing aromatic compounds, such as 2-vinylpyridine, 4-vinylpyridine and 4-vinylimidazole; and derivatives obtained by converting the above-mentioned vinyl compounds to a quarternary ammonium salt by the reaction with an alkyl halide or the like. However, the chemical species having basic functional groups employable in the present invention are not limited to the above-mentioned chemical species.

As examples of acidic functional groups usable in the present invention, there can be mentioned, for example, a carboxyl group, a phosphoric acid group, a sulfonic acid group and a phenol group. Examples of monomers having these functional groups include acrylic acid; methacrylic acid; 2-methacryloyloxyethylsuccinic acid; acrylic acid or methacrylic acid derivatives, such as mono(2-methacryloyloxyethyl)acid phosphate and 2-sulfoethyl methacrylate or the like; styrene derivatives, such as sodium p-styrene sulfonate; phenol derivatives such as vinyl phenol or the like; various vinyl monomers, e.g., allyl compounds, such as sodium allyl sulfonate; acetylene derivatives; and trioxane derivatives and the like. However, the chemical species having acidic functional groups employable in the present invention are not limited to the above-mentioned chemical species.

A fibrous, porous medium, such as a knit fabric, a woven fabric or a non-woven fabric, may be used as the porous element of the filter material of the present invention for selectively removing leukocytes. In this case, the fibrous, porous medium preferably has an average fiber diameter of 0.3 to 3.0 μm, more preferably 0.5 to 2.5 μm. When the fiber diameter of the fibrous, porous medium is more than 3.0 μm, the leukocyte removal efficiency of the filter material for selectively removing leukocytes is lowered on the other hand, when the average fiber diameter of the fibrous, porous medium is less than 0.3 μm, it is difficult to stably produce such a fibrous, porous medium, and the viscous resistance of blood becomes too high. The terminology "average fiber diameter" used in the present invention means a value obtained according to the following method. From one or more sheets of a fibrous body constituting the porous element, a portion of the fibrous body, which is recognized as being substantially uniform, is sampled out and the resultant sample is photographed by the use of for example, a scanning electron microscope. In the sampling, an effective filtering cross-sectional area portion of the fibrous body is sectioned into 0.5 cm×0.5 cm squares. From them, six squares are randomly sampled. In the random sampling, for example, an address is given to each of the above-mentioned square sections, and appropriate square sections are chosen, for example by a method in which the table of random numbers is used. In the photographing, a plurality of photographs are taken at the center portion and its neighborhood with respect to each of the sampled square sections. Photographing is continued until the number of fibers appearing in the photographs exceeds 100. The term "diameter" used herein means the width of a fiber as viewed in a direction perpendicular to the fiber axis. The average fiber diameter is the quotient of the sum of all measured fiber diameters divided by the number of fibers, provided that when a plurality of fibers overlap each other tothe fiby cause the measurement of the fiber width to be infeasible due to the shadowing of other fibers, when a plurality of fibers are formed into a thick fiber through melt adhesion or the like, or when fibers of markedly different diameters are mixed, measured data are omitted.

In general, blood products are roughly classified into a red cell product which contains a large amount of red cells, such as whole blood (WB) and concentrated red cells (CRC), and a platelet product which contains a large amount of platelets, such as platelet rich plasma (PRP) and platelet concentrate (PC). As mentioned above, each blood cell component is different in particle diameter and adherence, and the viscosity of blood is different according to the type of a blood product. Therefore, depending on the blood product to be treated by filteration, a filter material to be used for selectively removing leukocytes should be changed more or less with respect to the physical structure and chemical structure. Hereinbelow, explanation will be made on a filter material for selectively removing leukocytes from either red cell products or platelet products.

Red cell products, such as WB and CRC, are products each having a blood cell component content of about 40 to 70% and having a relatively high viscosity. In these blood products, about 60% of the contained leukocytes are granulocytes and monocytes, both of which are high in adherence and large in particle diameter, and about 40% of the leukocytes are lymphocytes which are low in adherence and small in particle diameter. When the filter material is to be used for selectively removing leukocytes from a red cell product while allowing red cells to pass therethrough, the porous element of the filter material has an average pore diameter of preferably 3 to 25 μm, more preferably 5 to 20 μm and has a total pore volume of 0.40 to 0.95 ml/ml of the porous element, wherein the sum of respective pore volumes of pores having a pore diameter of 2 to 30 μm is referably 85% or more, more preferably 90% or more, still more preferably 96% or more, based on the total pore volume. The porous element preferably has a total pore surface area of 0.50 to 5.70 $m^2$/ml of the porous element, wherein the sum of respective pore surface areas of pores having a pore diameter of 2 to 30 μm is preferably 50% or more, more preferably 60% or more, based on the total pore surface area. In the porous element, the sum of respective pore surface areas of pores having a pore diameter of 2 to 10 μm is preferably 35% or more, more preferably 45% or more, based on the total pore surface area. Red cells contained in red cell products have the high ability to exhibit metaboly, so that red cells can pass through even relatively small pores by virtue of metaboly. However, when red cells pass through pores each having a pore diameter of less than 2 μm, there is a danger of occurrence of an increase in the pressure loss due to the resistance to the passage of red cells. Therefore, in the porous element of the filter material for selectively removing leukocytes from a red cell product, the sum of respective pore volumes of pores having a pore diameter of less than 2 μm is preferably 8% or less, more preferably 5% or less, based on the total pore volume, and the sum of respective pore surface areas of pores having a pore diameter of less than 2 μm is preferably less than 40%, more preferably less than 30%, based on the total pore surface area. When the average pore diameter of the porous element is less than 3 μm, blood cells are likely to clog the porous element, and the resistance to the passage of red cells is increased, so that the pressure loss is likely to increase. When the average pore diameter of the porous element is more than 25 μm, the danger of leakage of leukocytes unfavorably increases. When the sum of respective pore volumes of pores having a pore diameter of 2 to 30 μm is less than 85%, based on the total pore volume, or when the sum of respective pore surface areas of pores having a pore diameter of 2 to 30 μm is less than 50%, based on the total pore surface area, it becomes difficult to remove leukocytes without causing a clogging and with a high efficiency such that the leukocyte residual ratio becomes $10^{-4}$ or less. Further, when the sum of respective pore volumes of pores having a pore diameter of less than 2 μm is more than 8%, based on the total pore volume, or when the sum of respective pore surface areas of pores having a pore diameter of less than 2 μm is 40% or more, based on the total pore surface area, not only is the rate of blood filtration unfavorably lowered due to the occurrence of clogging and of an increase in the pressure loss, but also the recovery of red cells unfavorably decreases.

It is preferred that the CWST value of the porous element of the filter material for removing leukocytes from a red cell product be 65 to 90 dyn/cm. When a basic functional group is introduced into a surface portion of the porous element, the porous element has, in the surface portion thereof, the basic functional group at a density of preferably $10^{-4}$ to 3 meq/$m^2$, more preferably $10^{-3}$ to 1 meq/$m^2$, most preferably $10^{-2}$ to $10^{-1}$ meq/$m^2$. When an acidic functional group is introduced into a surface portion of the porous element, the porous element has, in the surface portion thereof, the acidic functional group at a density of preferably $5\times 10^{-2}$ to 5 meq/$m^2$, more preferably $8\times 10^{-2}$ to 1 meq/$m^2$, most preferably $10^{-1}$ to $5\times 10^{-1}$ meq/$m^2$. The CWST values of most of ordinary synthetic polymer materials are 55 dyn/cm or less, so that wetting of a synthetic polymer material with blood is unlikely to occur. However, by the use of a porous element having its surface modified by graft polymerization, coating or the like so as to increase the CWST value to a level of from 65 to 90 dyn/cm, or by the use of a porous element which is formed of a polymer material having a hydrophilic functional group and has a CWST value within the above-mentioned range even without the surface modification, wetting of the porous element with blood is facilitated, so that a lowering of the filtration rate does not occur unless clogging occurs. Further, the introduction of a basic functional group or an acidic functional group into the surface portion of the porous element is also desirable because the leukocyte removal efficiency is improved due to the electrostatic interactions between the leukocytes and the surface of the porous element.

Platelet products, such as PRP and PC, are products characterized by having a low blood cell component content and consisting mostly of water. Therefore, these products have a relatively low viscosity. Further, about 90% of the leukocytes contained in a platelet product are of lymphocytes which are low in adherence and small in particle diameter. When the filter material is to be used for selectively removing leukocytes from a platelet product while allowing platelets to pass therethrough, the porous element of the filter material has an average pore diameter of preferably 1 to 15 μm, more preferably 2 to 12 μm and has a total pore volume of preferably 0.40 to 0.95 ml/ml of the porous element, wherein the sum of respective pore volumes of pores having a pore diameter of 1 to 25 μm is preferably 85% or more, more preferably 90% or more, based on the total pore volume. Further, the porous element has a total pore surface area of preferably 0.50 to 5.70 $m^2$/ml of the porous element, wherein the sum of respective pore surface areas of pores having a pore diameter of 1 to 25 μm is preferably 58% or more, more preferably 65% or more, based on the total pore surface area and the sum of respective pore surface areas of pores having a pore diameter of 1 to 10 μm is preferably 55% or more, based on the total pore surface area. Since most of leukocytes present in a platelet product are lymphocytes having a low adherence and a small particle diameter, pores having a pore diameter of more than 25 μm are substantially ineffective for the removal of leukocytes from a platelet product. For this reason, when the filter material is to be used for selectively removing leukocytes from a platelet product, in the porous element thereof, the sum of respective pore volumes of pores having a pore diameter of more than 25 μm is preferably 10% or less, more preferably 5% or less, based on the total pore volume, and the sum of respective pore surface areas of pores having a pore diameter of more than 25 μm is preferably 4% or less, more preferably 2% or less, based on the total pore surface area. When the average pore diameter is less than 1 μm, blood cells are likely to cause clogging and, in addition, there is a danger that platelets having a high adherence are removed by adhesion together with leukocytes. When the average pore diameter is more than 15 μm, a leakage of lymphocytes having a small particle diameter is likely to occur. Further, when the sum of respective pore volumes of pores having a pore diameter of 1 to 25 μm is less than 85%, based on the total pore volume, or when the sum of respective pore surface areas of pores having a pore diameter of 1 to 25 μm is less than 58%, based on the total pore surface area, it becomes difficult to remove leukocytes without causing clogging and with high efficiency such that the leukocyte residual ratio becomes $10^{-4}$ or less. Further, when the sum of respective pore surface areas of pores having a pore diameter of 1 to 10 μm is less than 55%, based on the total pore surface area, a leakage of lymphocytes is likely to occur, and likewise, when the sum of respective pore surface areas of pores having a pore diameter of more than 25 μm is more than 4%, based on the total pore surface area, a leakage of lymphocytes is likely to occur. The CWST value of the filter material for removing leukocytes from a platelet product is preferably 85 dyn/cm or more, more preferably 95 dyn/cm or more. In the case where a basic functional group is introduced into the surface portion of the porous element, the porous element has, in the surface portion thereof, the basic functional group at a density of preferably $10^{-6}$ to $10^{-1}$ meq/m$^2$, more preferably $10^{-5}$ to $10^{-1}$ meq/m$^2$, still more preferably $10^{-4}$ to $10^{-2}$ meq/m$^2$. In the case where an acidic functional group is introduced into the surface portion of the porous element, the porous element has, in the surface portion thereof, the acidic functional group at a density of preferably $10^{-4}$ to 1 meq/m$^2$, more preferably $5\times10^{-3}$ to $5\times10^{-1}$ meq/m$^2$, most preferably $5\times10^{-3}$ to $10^{-2}$ meq/m$^2$. When a platelet product is treated using either a porous element having its surface portion modified by graft polymerization, coating or the like to have a CWST value of 85 dyn/cm or more, or using a porous structure which is formed of a polymer material having a hydrophilic functional group and has a CWST value in the above-mentioned range even without surface modification, not only is wetting of the porous element with the platelet product facilitated, but also adhesion of platelets can advantageously be held down. Further, the introduction of a basic functional group or an acidic functional group into the surface portion of the porous element is also desirable because the leukocyte removal efficiency is improved due to the electrostatic interactions between the leukocytes and the surface of porous element, and the recovery of platelets can be increased. However, when the density of the basic functional group is less than $10^{-6}$ meq/m$^2$, or when the density of the acidic functional group is less than $10^{-4}$ meq/m$^2$, the improvement in the leukocyte removal efficiency becomes unsatisfactory. On the other hand, when the porous element has, in a surface portion thereof, a basic functional group at a density of more than $10^{-1}$ meq/m$^2$, or when the porous element has, in a surface portion thereof, an acidic functional group at a density of more than 1 meq/m$^2$, not only leukocytes but also platelets are likely to be unfavorably removed.

In another aspect of the present invention, there is provided a filter apparatus for selectively removing leukocytes from a leukocyte-containing suspension, which comprises a container having an inlet for a leukocyte-containing suspension and an outlet for a filtrate, and a porous structure packed in the container, the porous structure comprising a main porous element having an average pore diameter of 1 to 25 μm and a total pore volume of 0.40 to 0.95 ml/ml of the main porous element, wherein the sum of respective pore volumes of pores of the main porous element which have a pore diameter of 1 to 30 μm is 90% or more, based on the total pore volume.

With respect to the filter apparatus for selectively removing leukocytes according to the present invention, preferred conditions are set forth below:

(1) the main porous element has a total pore surface area of 0.50 to 5.70 m$^2$/ml of the main porous element, with the proviso that the sum of respective pore surface areas of pores of the main porous element which have a pore diameter of 1 to 30 μm is 60% or more, based on the total pore surface area;

(2) the sum of respective pore surface areas of pores of the main porous element which have a pore diameter of 1 to 10 μm is 50% or more, based on the total pore surface area;

(3) the porous structure further comprises at least one preliminary porous element (first stage leukocyte-capturing material) disposed upstream of the main porous element (second stage leukocyte-capturing material) with respect to a flow direction in which a leukocyte-containing suspension to be treated for removal of leukocytes is adapted to be flowed, the preliminary porous element having an average pore diameter which is larger than the average pore diameter of the main porous element so that the porous structure has an average pore diameter of 1 to 300 μm, and the porous structure has an average pore diameter gradient such that the average pore diameter is substantially continuously or stepwise decreased in the flow direction from an upstream end portion to a downstream end portion of the porous structure, the upstream end portion and the downstream end portion each having a thickness of 0.5 mm or less, as measured in a thicknesswise direction from the upstream end surface and from the downstream end surface of the porous structure, respectively;

(4) the upstream end portion of the porous sture hature has an average pore diameter of 10 to 300 μm and the downstream end portion of the porous structure has an average pore diameter of 1 to 25 μm, with the proviso that the average pore diameter of the upstream end portion of the porous structure is 2 to 100 times that of the downstream end portion of the porous structure; and/or (5) the preliminary porous element (first stage leukocyte-capturing material) is capable of capturing at least 60% of all leukocytes contained in the leukocyte-containing suspension;

(6) particularly when the leukocyte-containing suspension to be subjected to filtration is a leukocyte-containing red cell product;

(6-1) the main porous element has an average pore diameter of 3 to 25 µm, With the proviso that the sum of respective pore volumes of pores of the main porous element which have a pore diameter of 2 to 30 µm is 85% or more, based on the total pore volume, and that the sum of respective pore surface areas of pores of the main porous element which have a pore diameter of 2 to 30 µm is 50% or more, based on the total pore surface area, and the sum of respective pore surface areas of pores of the main porous element which have a pore diameter of 2 to 10 µm is 35% or more, based on the total pore surface area;

(6-2) the porous structure further comprises at least one preliminary porous element (first stage leukocyte-capturing material) disposed upstream of the main porous element (second stage leukocyte-capturing material) with respect to a flow direction in which a leukocyte-containing red cell product to be treated for removal of leukocytes is adapted to be flowed, the preliminary porous element having an average pore diameter which is larger than the average pore diameter of the main porous element so that the porous structure has an average pore diameter of 3 to 300 µm, and the porous structure has an average pore diameter gradient such that the average pore diameter is substantially continuously or stepwise decreased in the flow direction from an upstream end portion to a downstream end portion of the porous structure, the upstream end portion and the downstream end portion each having a thickness of 0.5 mm or less, as measured in a thicknesswise direction from the upstream end surface and from the downstream end surface of the porous structure, respectively;

(6-3) the upstream end portion of the porous structure has an average pose diameter of 15 to 300 µm and the downstream end portion of the porous structure has an average pore diameter of 3 to 25 µm, with the proviso that the average pore diameter of the upstream end portion is 3 to 100 times that of the downstream end portion of the porous structure; and/or (6-4) the preliminary porous element (first stage leukocyte-capturing material) is capable of capturing at least 60% of all leukocytes contained in said leukocyte-containing red cell product;

(7) particularly when the leukocyte-containing suspension is a leukocyte-containing platelet product;

(7-1) the main porous element has an average pore diameter of 1 to 15 µm, with the proviso that the sum of respective pore volumes of pores of the main porous element which have a pore diameter of 1 to 25 µm is 85% or more, based on the total pore volume, and that the sum of respective pore surface areas of pores of the main porous element which have a pore diameter of 1 to 25 µm is 58% or more, based on the total pore surface area, and the sum of respective pore surface areas of pores of the main porous element which have a pore diameter of 1 to 10 µm is 55% or more, based on the total pore surface area;

(7-2) the porous structure further comprises at least one preliminary porous element (first stage leukocyte-capturing material) disposed upstream of the main porous element (second stage leukocyte-capturing material) with respect to a flow direction in which a leukocyte-containing platelet product to be treated for removal of leukocytes is adapted to be flowed, the preliminary porous element having an average pore diameter which is larger than the average pore diameter of the main porous element so that the porous structure has an average pore diameter of 1 to 200 µm, and the porous structure has an average pore diameter gradient such that the average pore diameter is substantially continuously or stepwise decreased in the flow direction from an upstream end portion to a downstream end portion of the porous structure, the upstream end portion and the downstream end portion each having a thickness of 0.5 mm or less, as measured in a thicknesswise direction from the upstream end surface and from the downstream end surface of the porous structure, respectively;

(7-3) the upstream end portion of the porous structure has an average pore diameter of 10 to 200 µm and the downstream end portion of the porous structure has an average pore diameter of 1 to 15 µm, with the proviso that the average pore diameter of the upstream end portion of the porous structure is 2 to 60 times that of the downstream end portion of the porous structure;

(7-4) the preliminary porous element (first stage leukocyte-capturing material) is capable of capturing at least 60% of all leukocytes contained in the leukocyte-containing platelet product; and/or (7-5) the porous structure has a pore surface area of 0.01 to 0.08 m$^2$ per $2\times10^{10}$ platelets contained in the platelet product.

The above-mentioned main porous element of the porous structure to be packed in the container of the filter apparatus for selectively removing leukocytes according to the present invention corresponds to the porous element of the filter material for selectively removing leukocytes as described hereinbefore, which is provided according to the fundamental, primary aspect of the present invention. Therefore, the criticality and effect of each of the characteristics of the main porous element are substantially the same as described hereinbefore with respect to the porous element of the filter material.

In a preferred form of the filter apparatus for selectively removing leukocytes according to the present invention, as mentioned above, the porous structure comprises at least one preliminary porous element (first stage leukocyte-capturing material) disposed upstream of the main porous element (second stage leukocyte-capturing material) with respect to a flow direction in which a leukocyte-containing suspension to be treated for removal of leukocytes is adapted to be flowed. The above-mentioned preliminary porous element has preferably an average pore diameter which is larger than that of the main porous element so that the porous structure has an average pore diameter of 1 to 300 µm. Further, preferably, the porous structure has an average pore diameter gradient such that the average pore diameter is substantially continuously or stepwise decreased in the flow direction from an upstream end portion to a downstream end portion of the porous structure. The upstream end portion and the downstream end portion are defined as portions having a thickness of 0.5 mm or less, as measured in a thicknesswise direction from the upstream end surface and from the downstream end surface of the porous structure, respectively.

In the filter apparatus for selectively removing leukocytes according to the present invention, the terminology "substantially continuous decrease" used herein with respect to the average pore diameter of the porous structure means that the pore diameters of the porous structure are gradually decreased from an upstream end portion to a downstream end portion in a flow direction in which a leukocyte-containing suspension to be treated for removing leukocytes is adapted to be flowed. On the other hand, the terminology "stepwise decrease" used herein means that in the porous structure, there are thicknesswise extending portions, each of which contains pores having substantially the same average pore diameter, and the pore diameters of the porous structure are stepwise decreased from an upstream end portion to a downstream end portion in a flow direction in which a leukocyte-containing suspension to be treated for removing leukocytes is adapted to be flowed, through the above-mentioned portions having substantially the same average pore diameter. The above expression "substantially" implies that the decrease of the average pore diameter of the porous structure in a thicknesswise direction is not necessarily continuous or stepwise in the strict sense, as long as the average pore diameter is inclined to decrease in the approximate sense. When the average pore diameter is measured at three points or more, preferably five points or more, arbitrarily taken along the thicknesswise direction of the porous structure, followed by plotting of the average pore diameter (ordinate) against the thickness (abscissa) as measured from the upstream end surface of the porous structure, various patterns are obtained in the resultant graph. For example, there are obtained a pattern in which the average pore diameter is linearly decreased, a pattern in which the average pore diameter is decreased in a curve, and a pattern in which the average pore diameter is stepwise decreased. The terminology "decrease of the average pore diameter" used herein is intended to include all of such instances of decreases as represented by these patterns.

As in the case of the porous element of the leukocyte-removing filter material, the above-mentioned average pore diameter can be obtained by a method which comprises first cutting the porous structure in a direction perpendicular to a flow direction in which a leukocyte-containing suspension is adapted to be flowed to thereby obtain a cross-section, secondly identifying pores having substantially the same size which are most abundant among various pores distributed over the cross-section, and thirdly obtaining the pore size of the identified most abundant pores in terms of the diameter of a circle having the same area as the cross-sectional area of the identified pores. Illustratively stated, the pores distributed over an arbitrary cross-section of the porous structure may have various morphologies with various sizes. With respect to individual pores, respective cross-sectional areas are obtained in terms of respective diameters of circles having the same areas as the respective cross-sectional areas of the pores. When the number of the pores (ordinate) is plotted against the diameter (abscissa) of the corresponding circle, a nearly normal distribution curve is obtained. The average pore diameter used herein is defined as the diameter falling on the peak of the normal distribution curve. As apparent from the above, the average pore diameter represents an average diameter of the circles corresponding to the pores distributed over every arbitrary cross-section, and it is requisite in the present invention that the average pore diameter on any of the cross-sections be in the range of from 1 to 300 µm. In this connection, the average pore diameter of the porous structure can be measured by subjecting sampled portions each comprising the above-mentioned cross-section and having a thickness of not greater than 0.5 mm to mercury porosimetry (using Poresizer® 9320 of Shimazu Corporation, Japan) to be conducted in substantially the same manner as described hereinbefore with respect to the measurement of the porous element.

In the filter apparatus for selectively removing leukocytes according to the present invention, the upstream end portion and the downstream end portion of the porous structure are defined as portions each having a thickness of 0.5 mm or less, as measured in a thicknesswise direction from the upstream end surface and from the downstream end surface of the porous structure, respectively (hereinafter often referred to simply as "upstream end portion" and "downstream end portion", respectively). In the present invention, the surface area of the porous structure is the product of the specific surface area ($m^2/g$) of the porous structure measured by mercury porosimetry, multiplied by the bulk density ($g/cm^3$ or $g/ml$) of the porous structure. The above measurement by mercury porosimetry is made under substantially the same conditions as employed in actually packing the porous structure in the leukocyte-removing filter apparatus of the present invention.

With respect to the measurement by mercury porosimetry under a pressure using a mercury porosimeter, the pressure is in the same range of from 1 to 2650 psi as employed in the measurement of the porous element.

Further, in the filter apparatus for selectively removing leukocyte according to the present invention, it is preferred that the porous structure comprises a preliminary porous element (first stage leukocyte-capturing material) capable of capturing at least 60% of all leukocytes contained in a leukocyte-containing suspension, and the above-mentioned main porous element (second stage leukocyte-capturing material), the preliminary porous element being disposed upstream of the main porous element with respect to a flow direction in which the leukocyte-containing suspension is adapted to be flowed.

Preferred forms of the filter apparatus for selectively removing leukocytes according to the present invention will be described below.

As mentioned above, in the filter apparatus for selectively removing leukocytes according to the present invention, the porous structure preferably has at least one preliminary porous element (first stage leukocyte-capturing material) disposed upstream of the main porous element (second stage leukocyte-capturing material) with respect to a flow direction in which a leukocyte-containing suspension to be treated for removal of leukocytes is adapted to be flowed. The preliminary porous element preferably has an average pore diameter which is larger than that of the main porous element so that the porous structure has an average pore diameter of 1 to 300 µm. The porous structure preferably has an average pore diameter gradient such that the average pore diameter is substantially continuously or stepwise decreased in the flow direction from an upstream end portion to a downstream end portion of the porous structure. In a particular example of this preferred form of the filter apparatus, a fibrous medium or a spongy structure for capturing gels, microaggregates and the like contained in a blood product is disposed as an upper layer upstream of the main porous element. Further, between the material for capturing gels, microaggregates and the like, as mentioned above, and the main porous element as a leukocyte-removing filter material, another fibrous medium or spongy structure is preferably disposed as a first stage leukocyte-capturing material capable of capturing at least 60% of all leukocytes contained in a leukocyte-containing suspension.

A blood product is likely to contain gels, microaggregates (MA) and the like, in addition to blood cells, such as leukocytes, red blood cells and platelets, and plasma. In general, the gel has a diameter of 200 μm or less, and the MA has a diameter of 50 μm or less. The longer the blood product is preserved, the greater the number of gels and MA is likely to be. When leukocytes are removed from such preserved blood product containing gels andMAin large concentrations, it is necessary to consider clogging with the gels and MA. A leukocyte-removing filter apparatus which is effectively free from such a clogging with gels and MA, is obtained by disposing the above-mentioned fibrous medium or spongy structure upstream of the main porous element as a leukocyte-removing filter material. As a gel-capturing material, use is made of a fibrous medium comprising fibers having an average fiber diameter of 8 to 45 μm, preferably 10 to 32 μm, and more preferably 15 to 28 μm, and a spongy structure having an average pore diameter of 20 to 200 μm, preferably 25 to 180 μm. As an MA-capturing material, use is made of a fibrous medium, such as a knit fabric, a woven fabric and a non-woven fabric, each comprising fibers having an average fiber diameter of 3 μm or more, preferably 3 to 10 μm, and a spongy structure having an average pore diameter of 10 μm or more, preferably 10 to 50 μm.

As a preliminary porous element (first stage leukocyte-capturing material) to be disposed between the gel- and/or the MA-capturing material and the main porous element (second stage leukocyte-capturing material) as a leukocyte-removing filter material, use is made of a fibrous medium, such as a knit fabric, a woven fabric and a non-woven fabric, each comprising fibers having an average fiber diameter of 0.8 to 3 μm, and a spongy structure having an average pore diameter of 6 to 30 μm. In the first stage leukocyte-capturing material, the total pore volume of pores of the material and the total pore surface area of pores of the material are, at least 0.20 ml/ml of the material and at least 0.25 m²/ml, respectively, with the proviso that the sum of respective pore volumes of poles having a pore diameter of 1 to 30 μm suitable for capturing leukocytes is 35% or more, based on the total pore volume, and that the sum of respective pore surface areas of pores having a pore diameter of 1 to 30 μm is 40% or more.

Preferred as a fibrous medium to be used for the above-mentioned gel-capturing material is a needled fibrous web. The needled fibrous web has a structure in which the orientation of the fibers along the flow direction of the leukocyte-containing suspension is increased and, therefore, is different in structure from a plane-parallel fibrous medium having a structure in which the orientation of the fibers is high in a direction perpendicular to the flow direction of the leukocyte-containing suspension. When a fibrous medium comprised of the above-mentioned needled fibrous web is used as a gel-capturing material, gels are captured not only at a surface portion thereof but also at an inner portion thereof. Accordingly, the capacity of the fibrous medium for capturing gels per volume is higher than that of the plane-parallel fibrous medium in which gels are captured onlyat the upstream end surface thereof. By the use of the fibrous medium comprised of the needled fibrous web, it is feasible to reduce the amount of the gel-capturing material to be used, which is desired for obtaining a filter apparatus of small size having a decreased hold-up volume.

It is preferred that the pore surface area of the porous structure to be packed be increased in an exponential relationship from the upper stream end portion to the downstream end portion of the porous structure, to obtain a leukocyte-removing filter apparatus exhibiting an improved leukocyte removal efficiency without suffering from clogging of the porous structure. The reason for the preference is as follows. When the pore surface area of the upstream end portion of the porous structure is substantially the same as that of the downstream end portion of the porous structure, an extremely large number of leukocytes adhere to the surface of the upstream end portion, while leukocytes scarcely adhere to the surface of the downstream end portion, thereby causing clogging to be more likely to occur in the upstream end portion. Illustratively stated, when a leukocyte-containing suspension is passed through the porous structure, the concentration of leukocytes is decreased in an exponential relationship along a thicknesswise direction of the porous structure. Accordingly, for rendering the adhesion of leukocytes uniform along a thicknesswise direction of the porous structure to thereby minimize a clogging with leukocytes, it is effective and preferred to increase the pore surface area of the porous structure in an exponential relationship from the upstream end portion to the downstream end portion of the porous structure.

The filter material to be packed in the filter apparatus for selectively removing leukocytes according to the present invention preferably has a cross-sectional area for effective filtration of 1.0 to 100 cm² and a thickness of 0.05 to 100 mm.

By the use of a filter apparatus for selectively removing leukocytes according to the present Invention, in which a preliminary porous element as a first stage leukocyte-capturing material capable of capturing at least 60% of all leukocytes contained in a leukocyte-containing suspension to be filtered and a material capable of capturing gels and MAto inhibit a clogging with gels and MAare disposed upstream of the main porous element as a second stage leukocyte-capturing material, leukocytes can be removed in a high efficiency from the leukocyte-containing suspension, even if it is a suspension obtained from a preserved blood containing gels and MA in high concentrations, not only without suffering from a lowering of the filtering rate but also without suffering from a pressure loss increase.

The filter apparatus for selectively removing leukocytes according to the present invention is also intended to include filter apparatus other than mentioned above, as long as they are packed with the main porous element,having characteristics described as being essential to the present invention, even if any other materials are additionally contained. When the main porous element as the leukocyte-removing filter material of the present invention is packed in a filter apparatus, it is preferably disposed in the most downstream position with respect to a flow direction in which a leukocyte-containing suspension to be treated for removal of leukocytes is adapted to be flowed. The main porous element having characteristics described as being essential to the present invention is not limited with respect to the thickness, material and morphology.

When a fibrous medium is used as a leukocyte-capturing material according to the present invention, a gel-capturing material or an MA-capturing material, it is preferred that the fibrous medium be subjected to hot compression prior to being packed in a filter apparatus for selectively removing leukocytes. Hot compression is preferred for obtaining a filter apparatus having a small hold-up volume. Hot compression may be performed for example, by a method in which a fibrous medium subjected to external heating under a pressure, or a method in which a fibrous medium is heated from its inside by means of a high frequency microwave or the like under a pressure. The above-mentioned hot compression may be independently conducted with respect to each of the main porous element (second stage leukocyte-capturing material), the preliminary porous element (first stage leukocyte-capturing material) capable of capturing at least 60% of all leukocytes contained in a leukocyte-containing suspension, the gel-capturing material and the MA-capturing material. Alternatively, the hot compression may be simultaneously conducted with respect to two or more of the above-mentioned capturing materials.

When a blood product, such as whole blood, a red cell product and a platelet product, is filtered using the leukocyte-removing filter apparatus having the above-mentioned structure, since the pore diameter of the porous element is relatively large in an upstream position with respect to the flow direction of the leukocyte-containing suspension, the clogging of the porous structure with blood cells, gels and MA is alleviated, so that the blood cells can be passed through a porous channel. During the passage thereof, leukocytes gradually adhere to the surface of the porous structure and are hence removed so that the pressure loss in the filtration can be reduced.

The main porous element of the porous structure which is packed downstream with respect to the flow direction of the leukocyte-removing suspension in the filter apparatus for selectively removing leukocytes according to the present invention, corresponds to the porous element of the leukocyte-removing filter material provided according to a fundamental, primary aspect of the present invention, as mentioned above. The criticality and effect of each of the characteristics of the main porous element are substantially the same as described above with respect to the porous element of the leukocyte-removing filter material.

Hereinbelow, further explanation will be made with respect to a filter apparatus for selectively removing leukocytes as a preferred embodiment of the present invention, wherein the porous structure packed therein is comprised of at least one preliminary porous element (first stage leukocyte-capturing material) disposed upstream of a main porous element (second stage leukocyte-capturing material) with respect to a flow direction in which a leukocyte-containing suspension to be treated for removal of leukocytes is adapted to be flowed, the preliminary porous element having an average pore diameter which is larger than the average pore diameter of the main porous element so that the porous structure has an average pore diameter of 1 to 300 μm, and wherein the porous structure has an average pore diameter gradient such that the average pore diameter is substantially continuously or stepwise decreased in the flow direction from an upstream end portion to a downstream end portion of the porous structure. In this embodiment, the upstream end portion of the porous structure has preferably an average pore diameter of 10 to 300 μm, more preferably 10 to 150 μm, and most preferably 10 to 100 μm. When the average pore diameter of the upstream end portion of the porous structure is smaller than 10 μm, the filter material is likely to suffer from a clogging with blood cells during the leukocyte-removing filtration, thereby increasing the pressure loss. On the other hand, when the average pore diameter of the upstream end portion of the porous structure exceeds 300 μm, the frequency of the contact of blood cells with the surface of the filter material is likely to be decreased, so that the removal ratio of leukocytes on the surface of the filter material at the upstream end portion is decreased and the internal portion of the filter material is caused to suffer from a clogging with blood cells and the like. The downstream end portion of the porous structure has an average pore diameter of preferably 1 to 25 μm, more preferably 3 to 20 μm, and most preferably 5 to 18 μm. When the average pore diameter of the downstream end portion of the porous structure is smaller than 1 μm, the porous channel formed therein is likely to be too narrow, thereby increasing the pressure loss. On the other hand, when the average pore diameter of the downstream end portion df the porous structure exceeds 25 μm, theeamount of removed leukocytes is likely to be too small.

On the other hand, it is requisite that the downstream end portion (main porous element) of the porous structure have a total pore volume of 0.40 to 0.95 ml/ml of the main porous element, in which the sum of respective pore volumes of pores having a pore diameter of 1 to 30 μm be 90% or more, based on the total pore volume. The downstream end portion of the porous structure has a total pore surface area of preferably 0.50 to 5.70 $m^2$/ml of the main porous element, more preferably 0.70 to 5.70 $m^2$/ml of the main porous element, in which the sum of respective pore surface areas of pores having a pore diameter of 1 to 10 μm is preferably 50% or more, more preferably 55% or more, most preferably 60% or more, based on the total pore surface area of the downstream end portion of the porous structure and the sum of respective pore surface areas of podes having a pore diameter of 1 to 30 μm is preferably 60% or more, more preferably 65% or more, most preferably 70% or more, based on the total pore surface area of the downstream end portion. The sum of respective pore surface areas of pores having a pore diameter of less than 1 μm is preferably 38% or less, more preferably 30% or less, most preferably 28% or less. When the total pore surface area of the downstream end portion is less than 0.50 $m^2$/ml of the main porous element, the total pore surface area is insufficient for effective adhesion of leukocytes, thereby causing a leakage of leukocytes. On the other hand, when the total pore surface area of the downstream end portion exceeds 5.70 $m^2$/ml of the main porous element, the time necessary for the treatment of blood is prolonged, and not only leukocytes but also red cells and platelets are likely to be removed, so that the pressure loss is disadvantageously increased due to a clogging of the porous structure. Further, when the sum of respective pore surface areas of pores having a pore diameter of 1 to 10 μm and the sum of respective pore surface areas of pores having a pore diameter of 1 to 30 μm are, respectively, less than 50% and less than 60%, based on the total pore surface area of the downstream end portion of the porous structure, a leakage of lymphocytes or a clogging of the porous structure is likely to occur. Since pores having a pore diameter of less than 1 μm are less likely to allow passage of blood cells therethrough, when the sum of respective pore surface areas of pores having a pore diameter of less than 1 μm is more than 38%, the recoveries of red cells and platelets are disadvantageously lowered.

As mentioned above, in the downstream end portion (main porous element), the sum of respective pore volumes of pores having a pore diameter of 1 to 30 μm is 90% or more, based on the total pore volume, and it is preferred that the sum of respective pore volumes of pores having a pore diameter of more than 30 μm be 6% or less. The total pore volume is preferably 0.50 to 0.95 ml/ml of the main porous element, more preferably 0.60 to 0.95 ml/ml of the main porous element and, in the main porous element, the sum of respective pore volumes of pores having a pore diameter of 1 to 30 μm is preferably 95% or more, more preferably 98% or more, based on the total pore volume. The sum of respective pore volumes of pores having a pore diameter of more than 30 μm is preferably 4% or less, more preferably 2% or less. When the total pore volume is less than 0.40 ml/ml of the main porous element, the total pore volume is insufficient for effective passage of blood, therstr causing a clogging of the porous structure with blood cells. On the other hand, when the total pore volume is more than 0.95 ml/ml of the main porous element, the strength of the main porous element is too low, rendering it impossible for the main porous element to function as a filtering material. When the sum of respective pore volumes of pores having a pore diameter of 1 to 30 μm is less than 90%, based on the total pore volume, the main porous element is low in the amount of pores effective for removing leukocytes, thereby causing a leakage of leukocytes or a clogging of the porous structure with blood cells. On the other hand, when the sum of respective pore volumes of pores having a pore diameter of more than 30 μm is more than 6%, based on the total pore volume, the danger of occurrence of a leukocyte leakage is increased, thereby rendering it impossible to effectively remove leukocytes.

The upstream end portion of the porous structure has an average pore diameter which is preferably 2 to 100 times, more preferably 3 to 50 times, most preferably 3 to 25 times the average pore diameter of the downstream end portion of the porous structure. When the ratio of the average pore diameter of the upstream end portion to the average pore diameter of the downstream end portion is less than 2, a clogging of the porous structure with leukocytes and the like would occur. On the other hand, when the ratio of the average pore diameter of the upstream end portion to the average pore diameter of the downstream end portion is more than 100, a clogging of the porous structure with leukocytes and the like would occur in the downstream end portion, thereby increasing the pressure loss.

When a basic functional group is introduced into a surface portion of the porous structure, the density of the basic functional group in the surface portion of the porous structure is preferably $10^{-6}$ to 3 meq/m$^2$, more preferably $10^{-5}$ to 1 meq/m$^2$. When an acidic functional group is introduced into a surface portion of the porous structure, the density of the acidic functional group in the surface portion of the porous structure is preferably $10^{-4}$ to 5 meq/m$^2$, more preferably $5\times10^{-3}$ to 1 meq/m$^2$.

When the density of the basic functional group in the surface portion of the porous structure is less than $10^{-6}$ meq/m$^2$ or when the density of the adidic functional group in the surface portion of the porous structure is less than $10^{-4}$ meq/m$^2$, the electrostatic effect is likely to be unsatisfactory. On the other hand, when the density of the basic functional group in the surface portion of the porous structure is more than 3 meq/m$^2$ or when the density of the acidic functional group in the surface portion of the porous structure is more than 5 meq/m$^2$, the effect of the functional group would be exerted not only on leukocytes but also on other blood components, such as red cells and platelets, so that unfavorable phenomena, such as hemolysis, are likely to occur.

It is preferred that the porous structure used in the filter apparatus of the present invention for selectively removing leukocytes have a critical wetting surface tension (CWST) of at least 65 dyn/cm.

As mentioned above, the individual blood cell components are different from each other in particle diameter and adherence, and different types of blood products have different viscosities. Therefore, depending on the type of a blood product to be subjected to the leukocyte-removing treatment, the preferable average pore diameter and preferable pore diameter distribution of the porous structure may vary within the respective ranges defined in the present invention.

Hereinbelow, the present invention will be described, taking as example both the leukocyte-removing filter apparatus for a red cell product and the leukocyte-removing filter apparatus for a platelet product.

As mentioned above, red cell products, such as whole blood (WB) and concentrated red cells (CRC) are blood products which have a blood cell component content of about 40 to 70% and relatively high viscosities. Further, in these blood products, about 60% of the leukocytes contained is accounted for by granulocytes and monocytes, both of which are high in adherence and large in particle diameter, and the proportion of lymphocytes, which are low in adherence and small in particle diameter, is about 40%. When a porous structure is to be used for removing leukocytes from such a red cell product while allowing red cells to pass therethrough, the porous structure preferably has continuous pores having an average pore diameter of 3 to 300 μm, more preferably 3 to 200 μm, most more preferably 3 to 100 μm, and an average pore diameter gradient such that the average pore diameter is substantially continuously or stepwise decreased from the upstream end portion to the downstream end portion. The average pore diameter of the upstream end portion of the porous structure is preferably 15 to 300 μm, more preferably 15 to 200 μm and most preferably 15 to 100 μm, and the average pore diameter of the downstream end portion of the porous structure is preferably 3 to 25 μm, more preferably 5 to 20 μm. When the average pore diameter of the upstream end portion is less than 15 μm, a clogging of a surface of the porous structure is likely to occur, while when the average pore diameter of the upstream end portion is more than 300 μm, a clogging of the downstream end portion is likely to occur. When the average pore diameter of the downstream end portion is less than 3 μm, the pressure loss is likely to be increased, while when the average pore diameter of the downstream end portion is more than 25 μm, the amount of leukocytes to be removed is likely to be decreased. The upstream end portion of the porous structure has an average pore diameter which is preferably 3 to 100 times, more preferably 3 to 50 times, most preferably 3 to 25 times the average pore diameter of the downstream end portion (main porous element) of the porous structure. When the ratio of the average pore diameter of the upstream end portion to the average pore diameter of the downstream end portion is less than 3, a clogging of the porous structure is likely to occur. On the other hand, when the ratio of the average pore diameter of the upstream end portion to the average pore diameter of the downstream end portion is more than 100, a clogging of the porous structure is likely to occur, thereby increasing the pressure loss. The downstream end portion (main porous element) of the porous structure has a total pore volume of 0.40 to 0.95 ml/ml of the main porous element and, in the main porous element, the sum of respective pore volumes of pores having a pore diameter of 2 to 30 μm is preferably 85% or more, more preferably 90% or more, most preferably 96% or more, based on the total pore volume. The downstream end portion of the porous structure has a total pore surface area of preferably 0.50 to 5.70 m$^2$/ml of the main porous element, more preferably 0.80 to 5.70 m$^2$/ml of the main porous element and, in the downstream end portion, the sum of respective pore surface areas of pores having a pore diameter of 2 to 10 μm is preferably 35% or more, more preferably 45% or more, based on the total pore surface area of the downstream end portion and the sum of respective pore surface areas of pores having a pore diameter of 2 to 30 μm is preferably 50% or more, more preferably 60% or more, based on the total pore surface area of the downstream end portion. Red cells contained in a red cell product have a high ability to exhibit metaboly and hence can pass through relatively small pores by mixture of metaboly. However, when red cells pass through pores each having a pore diameter of less than 2 μm, there is a danger of occurrence of an increase in the pressure loss due to the resistance to the passage of red cells. Therefore, in the downstream end portion of the filter apparatus for selectively removing leukocytes from a red cell product, the sum of respective pore volumes of pores having a pore diameter of less than 2 μm is preferably 8% or less, more preferably 5% or less, based on the total pore volume, and the sum of respective pore surface areas of pores having a pore diameter of less than 2 μm is preferably less than 40%, more preferably less than 30%, based on the total pore surface area. When the sum of respective pore surface areas of pores having a pore diameter of 2 to 10 μm and the sum of respective pore surface areas of pores having a pore diameter of 2 to 30 μm are, respectively, less than 35% and less than 50%, based on the total pore surface are of the downstream end portion, the amount of leukocytes to be removed is likely to be decreased or a clogging of the porous structure is likely to occur. When the sum of respective pore surface areas of pores having a pore diameter of less than 2 μm is more than 40%, based on the total pore surface area, an increase in the pressure loss is likely to occur due to the resistance to the passage of red cells.

When the filter apparatus of the present invention is used for treating a red cell product, the CWST of the porous structure is preferably 65 to 90 dyn/cm. When a basic functional group is introduced into a surface portion of the porous structure, the density of the basic functional group in the surface portion is preferably $10^{-4}$ to 3 meq/m$^2$, more preferably $10^{-3}$ to 1 meq/m$^2$, most preferably $10^{-2}$ to $10^{-1}$ meq/m$^2$. When an acidic functional group is introduced into a surface portion of the porous structure, the density of the acidic functional group in the surface portion is preferably $5\times10^{-2}$ to 5 meq/m$^2$, more preferably $8\times10^{-2}$ to 1 meq/m$^2$, most preferably $10^{-1}$ to $5\times10^{-1}$ meq/m$^2$. When the density of the basic functional group in the surface portion of the porous structure is less than $10^{-4}$ meq/m$^2$ or when the density of the acidic functional group in the surface portion of the porous structure is less than $5\times10^{-2}$ meq/m$^2$, the improvement in the leukocyte removal efficiency is likely to be unsatisfactory. On the other hand, when the density of the basic functional group in the surface portion of the porous structure is more than 3 meq/m$^2$ or when the density of the acidic functional group in the surface portion of the porous structure is more than 5 meq/m$^2$, unfavorable phenomena, such as hemolysis are likely to occur.

Platelet products, such as platelet-rich plasma (PRP) and platelet concentrate (PC) are low in the content of the blood cell component, and substantially consist of water. Therefore, platelet products are relatively low in viscosity. Further, platelet products are characterized in that about 90% of the leukocytes contained therein is lymphocytes having low adherence and having a small particle diameter. When a porous structure is to be used for removing leukocytes from such a platelet product while allowing platelets to pass therethrough, the porous structure is desired to have continuous pores having an average pore diameter of preferably 1 to 200 μm, more preferably 1 to 100 μm, most preferably 2 to 50 μm, and to have an average pore diameter gradient such that the average pore diameter is substantially continuously or stepwise decreased from the upstream end portion to the downstream end portion. The average pore diameter of the upstream end portion of the porous structure is preferably 10 to 200 μm, more preferably 10 to 100 μm, most preferably 10 to 50 μm, and the average pore diameter of the downstream end portion of the porous structure is preferably 1 to 15 μm, more preferably 2 to 12 μm. The downstream end portion (main porous element) of the porous structure has a total pore volume of 0.40 to 0.95 ml/ml of the main porous element and, in the main porous element, the sum of respective pore volumes of pores having a pore diameter of 1 to 25 μm is preferably 85% or more, more preferably 90% or more, based on the total pore volume. When the average pore diameter of the upstream end portion is less than 10 μm, a clogging of a surface of the porous structure with blood cells and the like would occur, while when the average pore diameter of the upstream end portion is more than 200 μm, a clogging of the downstream end portion is likely to occur. When the average pore diameter of the downstream end portion is less than 1 μm, the pressure loss is likely to be increased, while when the average pore diameter of the downstream end portion is more than 15 μm, substantially no removal of lymphocytes is obtained. Thus, in the downstream end portion (main porous element) of the porous structure used in the filter apparatus for selectively removing leukocytes from a platelet product, the sum of respective pore volumes of pores having a pore diameter of more than 25 μm is preferably 10% or less, based on the total pore volume. The upstream end portion of the porous structure has an average bore diameter which is preferably 2 to 60 times, more preferably 2 to 30 times, most preferably 2 to 20 times the average pore diameter of the downstream end portion of the porous structure. When the ratio of the average pore diameter of the upstream end portion to the average pore diameter of the downstream end portion is less than 2, a clogging of the porous structure would occur or the amount of leukocytes to be removed would be decreased. On the other hand, when the ratio of the average pore diameter of the upstream end portion to the average pore diameter of the downstream end portion is more than 60, a clogging of the porous structure is likely to occur, thereby increasing the pressure loss. The downstream end portion of the porous structure preferably has a total pore surface area of 0.50 to 5.70 m$^2$/ml of the main porous element, more preferably 0.50 to 2.50 m$^2$/ml of the main porous element and, in the main porous element, the sum of respective pore surface areas of pores having a pore diameter of 1 to 10 μm is preferably 55% or more, more preferably 65% or more, based on the total pore surface area of the downstream end portion and the sum of respective pore surface areas of pores having a pore diameter of 1 to 25 μm is preferably 58% or more, more preferably 65% or more, based on the total pore surface area of the downstream end portion. In the downstream end portion of the porous structure, the sum of respective pore volumes of pores having a pore diameter of more than 25 μm is preferably 4% or less, more preferably 2% baseess, based on the total pore volume. Most of the leukocytes contained in a platelet product are lymphocytes having low adherence and having a small particle diameter, and a platelet product contains a large quantity of platelets having high adherence. Therefore, when the sum of respective pore surface areas of pores having a diameter of 1 to 10 μm and the sum of respective pore surface areas of pores having a diameter of 1 to 25 μm are, respectively, less than 55% and less than 58%, based on the total pore surface area of the downstream end portion, a leakage of lymphocytes is likely to occur. When the sum of respective pore surface areas of pores having a pore diameter of more than 25 μm is more than 4%, based on the total pore surface area, a leakage of lymphocytes is likely to occur. When the filter apparatus is used for treating a platelet product, the porous structure has a pore surface area of preferably 0.01 to 0.08 m², more preferably 0.02 to 0.08 m², most preferably 0.02 to 0.06 m² per $2\times10^{10}$ platelets contained in the platelet product. When the porous structure has a pore surface area of smaller than 0.01 m² per $2\times10^{10}$ platelets contained in the platelet product, the amount of leukocytes to be removed is too small, rendering it impossible to practically use the filter apparatus for treating a platelet product. On the other hand, when the porous structure has a pore surface area of larger than 0.08 m² per $2\times10^{10}$ platelets contained in the platelet product, platelets are likely to adhere to the porous structure, thereby lowering the recovery of platelets. The above-mentioned number of platelets "$2\times10^{10}$" corresponds to the number of platelets contained in 20 ml of platelet concentrate.

When the filter apparatus of the present invention is used for treating a platelet product, the CWST value of the porous structure is preferably 85 dyn/cm or more, more preferably 95 dyn/cm or more. When a basic functional group is introduced into a surface portion of the porous structure, the density of the basic functional group in the surface portion is preferably $10^{-6}$ to $10^{-1}$ meq/m², more preferably $10^{-5}$ to $10^{-1}$ meq/m², most preferably $10^{-4}$ to $10^{-2}$ meq/m². When an acidic functional group is introduced into a surface portion of the porous structure, the density of the acidic functional group in the surface portion is preferably $10^{-4}$ to 1 meq/m², more preferably $5\times10^{-3}$ to $5\times10^{-1}$ meq/m², most preferably $5\times10^{-3}$ to $10^{-2}$ meq/m². When a platelet product is treated by either a porous structure having its surface portion modified by graft polymerization, coating or the like to have a CWST value of 85 dyn/cm or more, or a porous structure which is formed from a polymer material having a hydrophilic functional group and has a CWST value in the above-mentioned range even without surface modification, not only is wetting of the porous structure with the platelet product facilitated, but also adherence of platelets can advantageously be decreased. Further, the introduction of a basic functional group or an acidic functional group into a surface portion of the porous structure improves not only the leukocyte removal efficiency by electrostatic interactions between leukocytes and the surface portion of the porous structure, but also the recovery of platelets. When the density of the basic functional group in the surface portion of the porous structure is less than $10^{-6}$ meq/m² or when the density of the acidic functional group in the surface portion of the porous structure is less than $10^{-4}$ meq/m², the improvement in the leukocyte removal efficiency is likely to be unsatisfactory. On the other hand, when the density of the basic functional group in the surface portion of the porous structure is more than $10^{-1}$ meq/m² or when the density of the acidic functional group in the surface portion of the porous structure is more than 1 meq/m², not only leukocytes but also platelets are likely to be removed.

As mentioned above, in general, the filter apparatus of the present invention for selectively removing leukocytes is advantageous not only in that the apparatus is compact and the pressure loss can be held down, but also in that a high leukocyte removal efficiency can be attained such that when a leukocyte-containing suspension is treated by the filter apparatus of the present invention, the leukocyte residual ratio is $10^{-4}$ or less. Particularly with respect to the performance of a filter apparatus of the present invention to be used for selectively removing leukocytes from a red cell product, it is desired that the leukocyte residual ratio be $10^{-4}$ or less, the red cell recovery be 90% or more and the pressure loss at the time of completion of the filtration be 150 mmHg or less. On the other hand, particularly with respect to the performance of a filter apparatus of the present invention to be used for selectively removing leukocytes from a platelet product, it is desired that the leukocyte residual ratio be $10^{-4}$ or less, the red cell recovery be 85% or more and the pressure loss at the time of completion of the filtration be 70 mmHg or less.

BEST MODE FOR CARRYING OUT THE INVENTION

Hereinbelow, the present invention will be illustrated with reference to Examples, which however should not be construed as limiting the present invention.

EXAMPLE 1

A hot-compressed non-woven fabric comprised of polyethylene terephthalate (PET) fibers having an average fiber diameter of 1.8 μm was packed into a container having a blood inlet and a blood outlet and having an effective filtration cross-sectional area of 4.9 cm×4.9 cm so that the thickness of the packed non-woven fabric (filter material) became 3.3 mm. The filter material in the resultant filter apparatus for selectively removing leukocytes was comprised of a porous element having an average pore diameter of 9.2 μm, a total pore volume of 0.85 ml/ml of the porous element and a total pore surface area of 0.95 m²/ml of the porous element. In the porous element, the sum of respective pore surface areas of pores having a diameter of 2 to 10 μm was 53%, based on the total pore surface area. The sum of respective pore volumes of pores having a pore diameter of 1 to 30 μm was 98%, based on the total pore volume and the sum of respective pore surface areas of the pores was 71%, based on the total pore surface area. The sum of respective pore volumes of pores having a pore diameter of 2 to 30 μm was 94%, based on the total pore volume and the sum of respective pore surface areas of the pores was 60%, based on the total pore surface area. The sum of respective pore volumes of pores having a pore diameter of larger than 30 μm was 1%, based on the total pore volume. The sum of respective pore surface areas of pores having a pore diameter of smaller than 1 μm was 28%, based on the total pore surface area. The sum of respective pore volumes of pores having a pore diameter of smaller than 2 μm was 5%, based on the total pore volume and the sum of respective pore surface areas of the pores was 39% of the total pore surface area.

513 ml of blood prepared by adding 63 ml of CPD (citrate phosphate dextrose) solution to 450 ml of whole blood was subjected to centrifugation within 8 hours after collection of the whole blood to separate 243 ml of platelet-enriched plasma from the whole blood, thereby obtaining a red cell product. The red cell product (hematocrit: 68%) was stored at 4° C. for 15 days, and then allowed to stand at room temperature (26° C.) until the temperature of the product reached 25° C. Then, the red cell product was filtered by a filter prepared by packing, into a container having an effective filtration cross-sectional area of 6.7 cm×6.7 cm, a needled fibrous web having an average fiber diameter of 20 μm as a gel-capturing material, a non-woven fabric comprised of fibers having an average fiber diameter of 3 μm as an MA-capturing material, and a non-woven fabric comprised of fibers having an average fiber diameter of 2.2 μm as a preliminary porous element (first stage leukocyte-capturing material). Thus, gel, MA and 90% of the leukocytes were removed from the red cell product. 200 ml of the thus treated red cell product was transferred to a fresh blood bag and filtered by the above-produced filter apparatus for selectively removing leukocytes.

The preparatory procedure before the filtration was performed by connecting the filter apparatus to the blood bag containing the red cell product through a blood circuit and manually applying pressure to the blood bag, thereby filling the filter apparatus with the blood. After filling the filter apparatus with the blood, the blood was caused to continuously flow at a constant rate of 4.5 ml/minute by means of PERISTA PUMP while measuring the pressure loss in the course of the filtration by means of a digital type pressure gauge. At the time when there was no longer blood in the blood bag, the filtration was completed, and the collection bag which had been connected to the downstream side of the filter apparatus through a blood circuit was cut off from the filter apparatus by cutting the blood circuit therebetween at a position 30 to 40 cm downstream of the blood outlet of the filter apparatus, thereby obtaining, as a collection liquid, the red cell product present in the collection bag and blood circuit.

The red cell product before filtration (hereinafter referred to as "pre-filtration liquid") and the collection liquid were measured with respect to the volume, the hematocrit and the number of leukocytes, thereby determining the red cell recovery and the leukocyte residual ratio.

Red Cell Recovery = [Collection Liquid Volume ×

Hematocrit(Collection Liquid)]/[Pre-filtration Liquid Volume ×

Hematocrit (Pre-filtration Liquid)].

Leukocyte Residual Ratio =

[Number of Leukocytes(Collection Liquid)]/

[Pre-filtration Liquid Volume ×

Leukocyte Concentration (Pre-filtration Liquid)].

With respect to the volumes of the pre-filtration liquid and the collection liquid, values obtained by dividing the weights of these liquids by 1.075 (a representative value of the specific gravity of a red cell product) were taken as the respective volumes. Further, the measurement of the leukocyte concentration of the pre-filtration liquid was performed by the following method.

The measurement of the leukocyte concentration of the pre-filtration liquid: A pre-filtration liquid diluted 10-fold with Türk's reagent was injected into a Burker-Türk type blood cell counting chamber and the leukocytes present in four major sections were counted through an optical microscope and the obtained number was taken as $n_{pre}$.

Leukocyte Concentration (before filtration) = $n_{pre} \times 0.25 \times 10^5$ cells/ml.

The measurement of the number of leukocytes contained in a collection liquid was performed by the extremely sensitive method described below.

An EBSS solution (hereinafter referred to as "FICOLL solution") containing 5% FICOLL 400 DL was introduced into a bag containing a collection liquid while shaking to facilitate mixing, the EBSS solution having an equivolume relative to the volume of the collection liquid. Then, the collection bag was fixed onto a plasma separation stand and allowed to stand still for 40 minutes. After that period, a supernatant was gently collected without disturbing a precipitated layer of red cells. Then, FICOLL was again introduced into the collection bag in the same volume as employed above, and the same procedure as described above was repeated. The supernatant collected by the collecting operation thus conducted twice was divided into four centrifuge tubes each being CORNING 25350 and centrifuged at 840× g for 15 minutes. Subsequently, the supernatant was discarded by means of an aspirator so carefully as not to withdraw the precipitate. 200 ml of a hemolysis solution (a 1.145% ammonium oxalate physiological saline solution) was introduced into each tube and the tubes were shaken to facilitate mixing, immediately followed by centrifugation at 468× g for 10 minutes. Subsequently, the supernatant was discarded by means of an aspirator while taking the same care as described above.

The precipitates in the four tubes were collected into a 15 ml centrifuge tube and a hemolysis solution was added thereto so that the total volume became 15 ml. The tube was allowed to stand still at room temperature for 10 minutes and then centrifuged at 468× g for 10 minutes. Part of the supernatant was carefully discarded so that the volume of the contents including the precipitates became 0.5 ml. The liquid in the tube containing the precipitates was stirred well to obtain a single cell suspension, and 50 μl of a fluorescent dyeing solution (69.9 mg/l Acridihe Orange) was added, followed by stirring. The resultant liquid was injected into six blood cell counting chambers of improved Neubauer type and the leukocytes present in 108 major sections were counted through an epi-fluorescence microscope.

From the resultant count ($n_{post}$) of leukocytes, the number of leukocytes (collection liquid) was calculated.

Number of Leukocytes (Collection Liquid) =

$\underline{n_{post} \times (1/108) \times 10^4} \times 0.55 \times (1/0.55)$.

The underlined portion in the formula represents the leukocyte concentration (cells/ml) in the liquid (hereinafter referred to as "concentrate") obtained by concentrating the collection liquid using a FICOLL solution to a total volume of 0.55 ml. The leukocyte concentration is multiplied by the volume of the concentrate (0.55 ml) to obtain the number of leukocytes. The reason why the thus obtained number of leukocytes is further divided by 0.55 is that the recovery of leukocytes attained by means of a FICOLL solution is 55%.

As a result of the above calculations, it was found that good results were obtained. That is, the red cell recovery was 95%, the leukocyte residual ratio was $10^{-4.2}$ and the pressure loss at the time of completion of the filtration was 103 mmHg.

COMPARATIVE EXAMPLE 1

A hot-compressed non-woven fabric comprised of polyethylene terephthalate (PET) fibers having an average fiber diameter of 1.8 μm was packed into a container having a blood inlet and a blood outlet and having an effective filtration cross-sectional area of 4.9 cm×4.9 cm so that the thickness of the packed non-woven fabric became 3.3 mm. The resultant filter material for removing leukocytes was comprised of a porous element having an average pore diameter of 14.2 μm, a total pore volume of 0.72 ml/ml of the porous element and a total pore surface area of 0.56 m²/ml of the porous element. In the porous element, the sum of respective pore surface areas of pores having a pore diameter of 2 to 10 μm was 29%, based on the total pore surface area. The sum of respective pore volumes of pores having a pore diameter of 1 to 30 μm was 78%, based on the total pore volume and the sum of respective pore surface areas of the pores was 56%, based on the total pore surface area. The sum of respective pore volumes of pores having a pore diameter of 2 to 30 μm was 74%, based on the total pore volume and the sum of respective pore surface areas of the pores was 34%, based on the total pore surface area. The sum of respective pore volumes of pores having a pore diameter of larger than 30 μm was 16%, based on the total pore volume. The sum of respective pore surface areas of pores having a pore diameter of smaller than 1 μm was 42%, based on the total pore surface area. The sum of respective pore volumes of pores having a pore diameter of smaller than 2 μm was 10%, based on the total pore volume and the sum of respective pore surface areas of the pores was 57%, based on the total pore surface area.

An experiment was conducted under substantially the same conditions as in Example 1 except that the above-obtained filter material was employed. As a result, with this filter material (which had a pore diameter distribution which was broad as compared to that of the filter material of the present invention and in which the sum of respective pore volumes of pores having a pore diameter of larger than 30 μm which are likely to cause a leakage of leukocytes was as large as 16%, based on the total pore volume), the leukocyte residual ratio was as high as $10^{-2.2}$. The red cell recovery was 91% and the pressure loss at the time of completion of the filtration was 118 mmHg, which were good.

EXAMPLE 2

Into a container having a blood inlet and a blood outlet and having an effective filtration cross-sectional area of 6.7 cm×6.7 cm was packed a porous structure comprised of a gel-capturing material, an MA-capturing material, a preliminary porous element (first stage leukocyte-capturing material) and a main porous element (second stage leukocyte-capturing material) according to the present invention, which were arranged from an upstream end portion to a downstream end portion with respect to a flow direction in which blood is adapted to be flowed, so that the total thickness of the porous structure became 5 mm. The gel-capturing material, the MA-capturing material, the preliminary porous element (first stage leukocyte-capturing material) and the main porous element (second stage leukocyte-capturing material) were substantially the same as employed in Example 1, which were hot-compressed beforehand. Thus, a filter apparatus for selectively removing leukocytes was prepared.

Through the thus prepared filter apparatus, a 0.5% ethanol solution of a polymer was flowed, which polymer was prepared from hydroxyethyl methacrylate (HEMA) and dimethylaminoethyl methacrylate (DM) (DM content of the polymer: 30% by mole), to thereby conduct a coating of the porous structure. Thereafter, nitrogen gas was passed, followed by drying under vacuum at 1 mmHg or less at 40° C. for 24 hours. After the drying, the main porous element was subjected to measuring with respect to a CWST value and a density of a basic functional group. Results showed that the CWST value was 80 dyn/cm and the basic functional group density was $4.8 \times 10^{-3}$ meq/m².

513 ml of blood prepared by adding 63 ml of CPD solution to 450 ml of whole blood was subjected to centrifugation within 8 hours after collection of the whole blood to separate 243 ml of platelet-enriched plasma from the whole blood, thereby obtaining a red cell product. The red cell product was stored at 4° C. for 3 days, and a physiological saline solution was added thereto so that the volume became 352 ml (hematocrit: 55%). The red cell product was allowed to stand at room temperature (26° C.) until the temperature of the product reached 25° C. Then, the red cell product was filtered by a blood circuit in which the above filter apparatus was incorporated. The filtering rate was constantly adjusted to 10 ml/min by means of PERISTA PUMP, while measuring the pressure loss in the course of the filtration by means of a digital type pressure gauge.

Results were excellent. That is, the red cell recovery was 92%, the leukocyte residual ratio was $10^{-5.2}$ and the pressure loss at the time of completion of the filtration was 132 mmHg.

COMPARATIVE EXAMPLE 2

The same gel-capturing material, MA-capturing material and preliminary porous element (first stage leukocyte-capturing material) as employed in Example 1 were packed into a container and, further, the same main porous element (second stage leukocyte-capturing material) as employed in Comparative Example 1 was disposed under the most downstream end portion of the capturing materials, so that the total thickness of the resultant porous structure became 5 mm (effective filtration cross-sectional area: 6.7 cm×6.7 cm). The individual capturing materials were hot-compressed in the same manner as in Example 2. Thus, a leukocyte removing filter apparatus was prepared. To the thus prepared filter apparatus was applied a coating of the same polymer (a polymer prepared from HEMA and DM, DM content thereof: 30% by mol) as employed in Example 2. The main porous element was found to have a CWST value of 80 dyn/cm and a density of basic functional group of $4.7 \times 10^{-3}$ meq/m².

An experiment was conducted under substantially the same conditions as in Example 2 except that the above-prepared filter apparatus was employed. Favorably, the red cell recovery was 90%, and the pressure loss at the time of completion of the filtration was 148 mmHg. However, unfavorably, the leukocyte removing efficiency of this filter apparatus was relatively low, and the leukocyte residual ratio was as large as 10–3.2.

COMPARATIVE EXAMPLE 3

The same gel-capturing material, MA-capturing material and preliminary porous element (first stage leukocyte-capturing material) as employed in Example 1 were packed into a container. Further, a non-woven fabric comprised of PET fibers having an average fiber diameter of 1.8 μm was disposed as a main porous element (second stage leukocyte-capturing material) under the most downstream end portion of the packing materials so that the total thickness of the resultant porous structure became 5 mm (effective filtration cross-sectional area: 6.7 cm×6.7 cm). The above capturing materials were hot-compressed in the same manner as in Example 2. The main porous element disposed at the most downstream end portion of the porous structure had an average pore diameter of 5.1 μm, a total pore volume of 0.37 ml/ml of the main porous element and a total pore surface area of 0.55 m²/ml of the main porous element. In the main porous element, the sum of respective pore surface areas of pores having a pore diameter of 2 to 10 μm was 33%, based on the total pore surface area. The sum of respective pore volumes of pores having a pore diameter of 1 to 30 μm was 87%, based on the total pore volume, and the sum of respective pore surface areas of such pores was 46%, based on the total pore surface area. The sum of respective pore volumes of pores having a pore diameter of 2 to 30 μm was 86%, based on the total pore volume, and the sum of respective pore surface areas of such pores was 35%, based on the total pore surface area. The sum of respective pore volumes of pores having a pore diameter of more than 30 μm was 1%, based on the total pore volume. The sum of respective pore surface areas of pores having a pore diameter of less than 1 μm was 53%, based on the total pore surface area. The sum of respective pore volumes of pores having a pore diameter of less than 2 μm was 13%, based on the total pore volume, and the sum of respective pore surface areas of such pores was 64%, based on the total pore surface area. The thus prepared filter apparatus for capturing leukocytes was subjected to a coating with the same polymer (a polymer prepared from HEMA and DM, DM content thereof: 30% by mol) as employed in Example 2. The main porous element was found to have a CWST value of 80 dyn/cm and a density of basic functional group of $4.8 \times 10^{-3}$ meq/m$^2$.

An experiment was conducted under substantially the same conditions as in Example 2 except that the above-prepared filter apparatus was employed, thereby finding that the leukocyte residual ratio was $10^{-4.8}$, which was a sufficient leukocyte removal efficiency. However, the total pore volume was small, and the sum of respective pore volumes of pores having a diameter of less than 2 μm through which it was difficult for blood cells to pass and the sum of respective surface areas of such pores were as high as 13% and 64%, respectively. Accordingly, the red cell recovery was as low as 79% and the pressure loss at the time of completion of the filtration was as high as not below 500 mmHg.

EXAMPLE 3

The same gel-capturing material, MA-capturing material and preliminary porous element (first stage leukocyte-capturing material) as employed in Example 1 were packed into a container and, further, a polyvinylformal(PVF)-made spongy structure having a three-dimensional network of continuous pores was disposed as a main porous element (second stage leukocyte-capturing material) under the most downstream end portion of the capturing materials so that the total thickness of the resultant porous structure became 4 mm (effective filtration cross-sectional area: 6.7 cm×6.7 cm). The above-mentioned gel-capturing material, MA-capturing material and preliminary porous element (first stage leukocyte-capturing material) were subjected to preliminarymolding by hot compression in the same manner as in Example 2.

The main porous element disposed at the most downstream end portion of the porous structure had an average pore diameter of 9.4 μm, a total pore volume of 0.90 ml/ml of the main porous element, and a total pore surface area of 0.81 m$^2$/ml of the main porous element. In the main porous element, the sum of respective pore surface areas of pores having a pore diameter of 2 to 10 μm was 55%, based on the total pore surface area. The sum of respective pore volumes of pores having a pore diameter of 1 to 30 μm was 98%, based on the total pore volume, and the sum of respective pore surface areas of such pores was 73%, based on the total pore surface area. The sum of respective pore volumes of pores having a pore diameter of 2 to 30 μm was 96%, based on the total pore volume, and the sum of respective pore surface areas of such pores was 61%, based on the total pore surface area. The sum of respective pore volumes of pores having a pore diameter of more than 30 μm was 2%, based on the total pore volume. The sum of respective surface areas of pores having a pore diameter of less than 1 μm was 26%, based on the total pore surface area. The sum of respective pore volumes of pores having a pore diameter of less than 2 μm was 4%, based on the total pore volume, and the sum of respective pore surface areas of such pores was 38%, based on the total pore surface area. The resultant leukocyte removing filter apparatus was subjected to a coating with the same polymer (a polymer prepared from HEMA and DM, DM content thereof: 30% by mol) as in Example 2. Thus, the main porous element was found to have a CWST value of 82 dyn/cm and a density of basic functional group of $4.7 \times 10^{-3}$ meq/m$^2$.

An experiment was conducted under substantially the same conditions as in Example 2 except that the thus prepared filter apparatus was employed. Favorable results were obtained. That is, the red cell recovery was 95%, the leukocyte residual ratio was $10^{-5.1}$ and the pressure loss at the time of completion of the filtration was 108 mmHg.

COMPARATIVE EXAMPLE 4

The same gel-capturing material, MA-capturing material and preliminary porous element (first stage leukocyte-capturing material) as employed in Example 1 were packed into a container and, further, a PVF-made spongy structure was disposed as a main porous element under the most downstream end portion of the capturing materials so that the total thickness of the resultant porous structure became 4 mm (effective filtration cross-sectional area: 6.7 cm×6.7 cm). The above-mentioned gel-capturing material, MA-capturing material and preliminary porous element (first stage leukocyte-capturing material) were hot-compressed in the same manner as in Example 2. The main porous element disposed at the most downstream end portion of the porous structure had an average pore diameter of 8.0 μm, a total pore volume of 0.41 ml/ml of the main porous element and a total pore surface area of 0.59 m$^2$/ml of the main porous element. In the main porous element, the sum of respective pore surface areas of pores having a pore diameter of 2 to 10 μm was 35%, based on the total pore surface area. The sum of respective pore volumes of pores having a pore diameter of 1 to 30 μm was 81%, based on the total pore volume, and the sum of respective pore surface areas of such pores was 54%, based on the total pore surface area. The sum of respective pore volumes of pores having a pore diameter of 2 to 30 μm was 78%, based on the total pore volume, and the sum of respective pore surface areas of such pores was 41%, based on the total pore surface area. The sum of respective pore volumes of pores having a pore diameter of more than 30 μm was 9%, based on the total pore volume. The Sum of respective pore surface areas of pores having a pore diameter of less than 1 μm was 44%, based on the total pore surface area. The sum of respective pore volumes of pores having a pore diameter of less than 2 μm was 13%, based on the total pore volume, and the sum of respective pore surface areas of such pores was 57%, based on the total pore surface area. The thus-prepared filter apparatus for removing leukocytes was subjected to a coating with the same polymer (a polymer prepared from HEMA and DM, DM content thereof: 30% by mol) as in Example 2. Thus, the main porous element was found to have a CWST value of 82 dyn/cm and a density of basic functional group of $4.6 \times 10^{-3}$ meq/m$^2$.

An experiment was conducted under substantially the same conditions as in Example 2 except that the above prepared filter apparatus was employed. As a result, it was found that the red cell recovery was as good as 89%. However, the sum of respective pore volumes of pores having a pore diameter of less than 2 μm through which it was difficult for leukocytes to pass and the sum of respective pore surface areas of such pores were as relatively large as 13% and 57%, respectively, and the sum of respective pore volumes of pores having a pore diameter of more than 30 μm at which leakage of leukocytes occurred was as relatively large as 9%. Thus, the leukocyte residual ratio was found to be $10^{-3.4}$, showing that the leukocyte removal efficiency was comparatively inferior. Further, the pressure loss at the time of completion of the filtration was found to be as high as 205 mmHg.

COMPARATIVE EXAMPLE 5

The same gel-capturing material, MA-capturing material and preliminary porous element (first stage leukocyte-capturing material) as employed in Example 1 were packed into a container and, further, a PVF-made spongy structure was disposed as a main porous element (second stage leukocyte-capturing material) under the most downstream end portion of the capturing materials so that the total thickness of the resultant porous structure became 4 mm (effective filtration cross-sectional area: 6.7 cm×6.7 cm). The above-mentioned gel-capturing material, MA-capturing material and preliminary porous element (first stage leukocyte-capturing material) were hot-compressed in the same manner as in Example 2. The main porous element disposed under the most downstream end portion of the porous structure had an average pore diameter of 25.4 μm, a total pore volume of 0.55 ml/ml of the main porous element and a total pore surface area of 0.60 m²/ml of the main porous element. In the main porous element, the sum of respective pore surface areas of pores having a pore diameter of 2 to 10 μm was 41%, based on the total pore surface area. The sum of respective pore volumes of pores having a pore diameter of 1 to 30 μm was 70%, based on the total pore volume and the sum of respective pore surface areas of such pores was 58%, based on the total pore surface area. The sum of respective pore volumes of pores having a pore diameter of 2 to 30 μm was 69%, based on the total pore volume, and the sum of respective pore surface areas of such pores was 46%, based on the total pore surface area. The sum of respective pore volumes of pores having a pore diameter of more than 30 μm was 28%, based on the total pore volume. The sum of respective pore surface areas of pores having a pore diameter of less than 1 μm was 33%, based on the total pore surface area. The sum of respective pore volumes of pores having a pore diameter of less than 2 μm was 3%, based on the total pore volume, and the sum of respective pore surface areas of such pores was 46%, based on the total pore surface area. The resultant filter apparatus for removing leukocytes was coated with the same polymer (a polymer prepared from HEMA and DM, DM content thereof: 30% by mol) as in Example 2. Thus, the main porous element was found to have a CWST value of 82 dyn/cm and a density of basic functional group of $4.8 \times 10^{-3}$ meq/m². An experiment was conducted under substantially the same conditions as in Example 2 except that the above prepared filter apparatus was employed. As a result, it was found that the red cell recovery was as high as 97% and the pressure loss at the time of completion of the filtration was as low as 51 mmHg. However, the sum of respective pore volumes of pores having a pore diameter of more than 30 μm at which leakage of leukocytes occurred was as large as 28%, and the average pore diameter was as relatively large as 25.4 μm. Therefore, the leukocyte residual ratio was $10^{-1.4}$, showing that the leukocyte removal efficiency of the filter apparatus was poor.

EXAMPLE 4

Into a container having a blood inlet and a blood outlet and having an effective filtration cross-sectional area of 3.0 cm×3.0 cm were packed a needled fibrous web comprised of fibers having an average fiber diameter of 15 μmas a gel-capturing material, a non-woven fabric comprised of fibers having an average fiber diameter of 3 μm as an ariMA-capturing material and a non-woven fabric comprised of fibers having an average fiber diameter of 2.2 μm as a preliminary porous element (first stage leukocyte-capturing material). Under the most downstream end portion of capturing materials, a non-woven fabric comprised of fibers having an average fiber diameter of 1.2 μm was disposed as a main porous element (second stage leukocyte-capturing material), so that the total thickness of the resultant porous structure became 5 mm. The gel-capturing material, the MA-capturing material, the preliminary porous element and the main porous element were hot-compressed beforehand. The main porous element disposed at the most downstream end portion of the porous structure was comprised of PET fibers, having an average pore diameter of 9.2 μm, a total pore volume of 0.83 ml/ml of the main porous element and a total pore surface area of 1.02 m²/ml of the main porous element. In the main porous element, the sum of respective pore surface areas of pores having a pore diameter of 1 to 10 μm was 63%, based on the total pore surface area. The sum of respective pore volumes of pores having a pore diameter of 1 to 30 μm was 95%, based on the total pore volume, and the sum of respective pore surface areas of such pores was 72%, based on the total pore surface area. The sum of respective pore volumes of pores having a pore diameter of 1 to 25 μm was 92%, based on the total pore volume, and the sum of respective pore surface areas of such pores was 71%, based on the total pore surface area. The sum of respective pore volumes of pores having a pore diameter of more than 30 μm was 2%, based on the total pore volume. The sum of respective pore surface areas of pores having a pore diameter of less than 1 μm was 27%, based on the total pore surface area. The sum of respective pore volumes of pores having a pore diameter of more than 25 μm was 5%, based on the total pore volume, and the sum of respective pore surface areas of such pores was 2%, based on the total pore surface area. Through the resultant filter apparatus for selectively removing leukocytes, a 1.0% ethanol solution of polymer was flowed, which polymer was prepared from HEMA and DM (DM content of the polymer: 3% by mole), to thereby coat the porous structure. Thereafter, nitrogen gas was passed, followed by drying under a vacuum of 1 mmHg at 40° C. for 24 hours. After the drying, the porous structure was subjected to measurement with respect to a CWST value and a density of a basic functional group. Results showed that the main porous element had a CWST value of 102 dyn/cm and a density of basic nitrogen-containing functional group of $9.5 \times 10^{-4}$ meq/m².

230 ml of a platelet concentrate (to which 30 ml of CPD solution had been added) as a platelet product was stored at room temperature while shaking for two days, and filtered using a blood circuit in which the above filter apparatus was incorporated. For starting the filtration, the filter apparatus was connected to a blood bag containing the platelet produce through a blood circuit to thereby fill the filter apparatus with the platelet product. After the filling of the filter apparatus, the platelet product was caused to continuously flow at a constant rate of 5 ml/min by means of PERISTA PUMP, while measuring the pressure loss in the course of the filtration by means of a digital type pressure gauge. At the time when there was no longer platelet product in the blood bag, the filtration was completed. The collection bag which had been connected to the downstream end portion of the filter apparatus through a blood circuit was cut off from the filter apparatus by cutting the blood circuit therebetween at a position 30 to 40 cm downstream of the blood outlet of the filter apparatus, thereby obtaining, as a collection liquid, the platelet product present in the collection bag and blood circuit.

The platelet product before filtration (hereinafter referred to as "pre-filtration liquid") and the collection liquid were measured with respect to the volume, the number of platelets and the number of leukocytes, thereby determining the platelet recovery and the leukocyte residual ratio.

Platelet Recovery={(Collection Liquid volume×Platelet Concentration (Collection Liquid)}/{Pre-filtration Liquid volume×Platelet Concentration (Prefiitration Liquid)}

Leukocyte Residual Ratio={Number of Leukocytes (Collection Liquid)}/{(Pre-filtration Liquid volume)×Leukocyte Concentration (Pre-filtration Liquid)}

With respect to the volumes of the pre-filtration liquid and the collection liquid, values obtained by dividing the weights of these liquids by 1.030 (a representative value of the specific gravity of a platelet product) were taken as the respective volumes. Further, the measurement of the leukocyte concentration was performed by the following method.

The measurement of the leukocyte concentration of the pre-filtration liquid: A pre-filtration liquid diluted 10-fold with Türk's reagent was injected into a Burker-Türk type hemocytometer, and the leukocytes present in eight major sections were counted through an optical microscope and the obtained number was taken as $n_{pre}$.

Leukocyte Concentration (Pre-filtration)=$n_{pre}$×⅛×10⁵/ml.

The measurement of the number of leukocytes contained in the collection liquid was performed by the extremely sensitive method which was equivalent to the method in Example 1.

The measurement of the platelet concentration was performed by measuring species diluted 250,000-fold by means of an automatic blood cell counter.

As a result, it was found that the platelet recovery was as excellent as 93%, that the leukocyte residual ratio was as excellent as $10^{-5.0}$, and that the pressure loss at the time of completion of the filtration was as excellent as 48 mmHg. The surface area of the porous structure as required for treating platelets was 0.072 m² per 2×10¹⁰ platelets.

COMPARATIVE EXAMPLE 6

The same cell-capturing material, MA-capturing material and preliminary porous element (first stage leukocyte-capturing material) as employed in Example 3 were packed into a container. Further, a non-woven fabric comprised of PET fibers having an average fiber diameter of 1.2 μm was disposed as a main porous element (second stage leukocyte-capturing material) under the most downstream end portion of the capturing materials so that the total thickness of the resultant porous structure became 4 mm (effective filtration cross-sectional area: 3.0 cm×3.0 cm). The above capturing materials were hot-compressed in the same manner as in Example 1. The main porous element disposed at the most downstream end portion of the porous structure had an average pore diameter of 10.6 μm, a total pore volume of 0.79 ml/ml of the main porous element and a total pore surface area of 0.58 m²/ml of the main porous element. In the main porous element, the sum of respective pore surface areas of pores having a pore diameter of 1 to 10 μm was 44%, based on the total pore surface area. The sum of respective pore volumes of pores having a pore diameter of 1 to 30 μm was 84%, based on the total pore volume, and the sum of respective pore surface areas of such pores was 54%, based on the total pore surface area. The sum of respective pore volumes of pores having a pore diameter of 1 to 25 μm was 80%, based on the total pore volume, and the sum of respective pore surface areas of such pores was 53%, based on the total pore surface area. The sum of respective pore volumes of pores having a pore diameter of more than 30 μm was 8%, based on the total pore volume. The sum of respective pore surface areas of pores having a pore diameter of less than 1 μm was 42%, based on the total pore surface area. The sum of respective pore volumes of pores having a pore diameter of more than 25 μm was 14%, based on the total pore volume, and the sum of respective pore surface areas of such pores was 5%, based on the total pore surface area. The resultant leukocyte-removing filter apparatus was also subjected to a coating with 15 the same polymer (a polymer prepared from HEMA and DM, DM content thereof: 3% by mole) as in Example 4. The main porous element was found to have a CWST value of 102 dyn/cm and a density of basic functional group of 9.6×10⁻⁴ meq/m². An experiment was conducted under substantially the same conditions as in Example 4. As a result, it was found that the platelet recovery was as good as 87%. However, the sum of respective pore volumes of pores having a pore diameter of more than 25 μm at which leakage of leukocytes occurred and the sum of respective pore surface areas of such pores were as relatively large as 14% and 5%, respectively. Accordingly, the leukocyte residual ratio was $10^{-2.9}$, showing that the leukocyte removal efficiency was relatively poor, and the pressure loss at the time of completion of the filtration was unfavorably as high as 85 mmHg. The surface area of the porous structure as required for treating platelets was 0.056 m² per 2×10¹⁰ platelets.

COMPARATIVE EXAMPLE 7

The same gel-capturing material, MA-capturing material and preliminary porous element (first stage leukocyte-capturing material) as employed in Example 3 were packed into a container. Further, a non-woven fabric comprised of PET fibers having an average fiber diameter of 1.2 μm was disposed as a main porous element (second stage leukocyte-capturing material) under the most downstream end portion of the capturing materials so that the total thickness of the resultant porous structure became 4 mm (effective filtration cross-sectional area: 3.0 cm×3.0 cm). The above-mentioned individual capturing materials were hot-compressed in the same manner as in Example 1.

The main porous element disposed at the most downstream end portion of the porous structure had an average pore diameter of 16.2 μm, a total pore volume of 0.86 ml/ml of the main porous element and a total pore surface area of 0.51 m²/ml of the main porous element. In the main porous element, the sum of respective pore surface areas of pores having a pore diameter of 1 to 10 μm was 39%, based on the total pore surface area. The sum of respective pore volumes of pores having a pore diameter of 1 to 30 μm was 77%, based on the total pore volume, and the sum of respective pore surface areas of such pores was 51%, based on the total pore surface area. The sum of respective pore volumes of pores having a pore diameter of 1 to 25 μm was 71%, based on the total pore volume, and the sum of respective pore surface areas of such pores was 49%, based on the total pore surface area. The sum of respective pore volumes of pores having a pore diameter of larger than 30 μm was 20%, based on the total pore volume. The sum of respective pore surface areas of pores having a pore diameter of smaller than 1 μm was 40%, based on the total pore surface area. The sum of respective pore volumes of pores having a pore diameter of larger than 25 μm was 26%, based on the total pore volume, and the sum of respective pore surface areas of such pores was 11%, based on the total pore surface areas. To the resultant leukocyte-removing filter apparatus was applied a coating of the same polymer prepared from HEMA and DM (DM content thereof: 3% by mole) as in Example 4. The above main porous element had a CWST value of 102 dyn/cm and a density of basic functional group of $9.4 \times 10^{-4}$ meq/m$^2$.

An experiment was conducted under substantially the same conditions as in Example 4 except that the above-mentioned filter apparatus was employed. Good results were obtained with respect to the platelet recovery and the pressure loss at the time of completion of the filtration, which were 98% and 26 mmHg, respectively. However, the leukocyte removal efficiency of this filter apparatus was poor, because the sum of respective pore volumes of pores of the main porous element having a pore diameter of larger than 25 μm at which a leakage of leukocytes occurred was as large as 26%, based on the total pore volume, and the sum of respective pore surface areas of such pores was as large as 11%, based on the total pore surface area, and because the average pore diameter of the main porous element was as relatively large as 16.2 μm. The leukocyte residual ratio was $10^{-0.8}$, showing a poor leukocyte residual ratio. The pore surface area of the porous structure as required for treating platelets was 0.045 m$^2$ per $2 \times 10^{10}$ platelets.

EXAMPLE 5

The same gel-capturing material, MA-capturing material and preliminary porous element (first stage leukocyte-capturing material) as employed in Example 1 were packed into a container. Further, a spongy structure having a three-dimensional network of continuous pores which was comprised of PU fibers was disposed as a main porous element (second stage leukocyte-capturing material) under the most downstream end portion of the capturing materials so that the total thickness of the resultant porous structure became 3 mm (effective filtration cross-sectional area: 6.7 cm×6.7 cm). The above-mentioned individual capturing materials were hot-compressed in the same manner as in Example 1.

The main porous element disposed at the most downstream end portion of the porous structure had an average pore diameter of 7.4 μm, a total pore volume of 0.73 ml/ml of the main porous element and a total pore surface area of 0.94 m$^2$/ml of the main porous element. In the main porous element, the sum of respective pore surface areas of pores having a pore diameter of 1 to 10 μm was 60%, based on the total pore surface area. The sum of respective pore volumes of pores having a pore diameter of 1 to 30 μm was 96%, based on the total pore volume, and the sum of respective pore surface areas of such pores was 66%, based on the total pore surface area. The sum of respective pore volumes of pores having a pore diameter of 1 to 25 μm was 94%, based on the total pore volume, and the sum of respective pore surface areas of such pores was 65%, based on the total pore surface area. The sum of respective pore volumes of pores having a pore diameter of larger than 30 μm was 1%, based on the total pore volume. The sum of respective pore surface areas of pores having a pore diameter of smaller than 1 μm was 34%, based on the total pore surface area. The sum of respective pore volumes of pores having a pore diameter of larger than 25 μm was 3%, based on the total pore volume, and the sum of respective pore surface areas of pores having a pore diameter of larger than 25 μm was 1%, based on the total pore surface area. To the resultant filter apparatus for selectively removing leukocytes was applied a coating of the same polymer prepared from HEMA and DM (DM content thereof: 3% by mole) as in Example 4. The above main porous element had a CWST value of 102 dyn/cm and a density of basic functional group of $9.6 \times 10^{-4}$ meq/m$^2$.

An experiment was conducted under substantially the same conditions as in Example 4 except that the above filter apparatus was employed. Excellent results were obtained with respect to the platelet recovery, the leukocyte residual ratio and the pressure loss at the time of completion of the filtration, which were 95%, $10^{5.3}$ and 62 mmHg, respectively. The surface area of the main porous element as required for treating platelets was 0.070 m$^2$ per $2 \times 10^{10}$ platelets.

COMPARATIVE EXAMPLE 8

The same gel-capturing material, MA-capturing material and preliminary porous element (first stage leukocyte-capturing material) as employed in Example 1 were packed into a container. Further, a spongy structure comprised of PU fibers was disposed as a main porous element (second stage leukocyte-capturing material) under the most downstream end portion of the capturing materials so that the total thickness of the resultant porous structure became 3 mm (effective filtration cross-sectional area: 3.0 cm×3.0 cm). The above-mentioned individual capturing materials were hot-compressed in the same manner as in Example 1.

The main porous element disposed at the most downstream end portion of the porous structure had an average pore diameter of 8.1 μm, a total pore volume of 0.58 ml/ml of the main porous element and a total pore surface area of 0.78 m$^2$/ml of the main porous element. In the main porous element, the sum of respective pore surface areas of pores having a pore diameter of 1 to 10 μm was 41%, based on the total pore surface area. The sum of respective pore volumes of pores having a pore diameter of 1 to 30 μm was 81%, based on the total pore volume, and the sum of respective pore surface areas of such pores was 50%, based on the total pore surface area. The sum of respective pore volumes of pores having a pore diameter of 1 to 25 μm was 79%, based on the total pore volume, and the sum of respective pore surface areas of such pores was 48%, based on the total pore surface area. The sum of respective pore volume's of pores having a pore diameter of larger than 30 μm was 10%, based on the total pore volume. The sum of respective pore surface areas of pores having a pore diameter of smaller than 1 μm was 47%, based on the total pore surface area. The sum of respective pare volumes of pores having a pore diameter of larger than 25 μm was 12%, based on the total pore volume, and the sum of respective pore surface areas of such pores was 5%, based on the total pore surface area. To the resultant leukocyte-removing filter apparatus was applied a coating of the same polymer prepared from HEMA and DM (DM content thereof: 3% by mole) as in Example 4. The above main porous element had a CWST value of 102 dyn/cm and a density of basic functional group of $9.4 \times 10^{-4}$ meq/m$^2$.

An experiment was conducted under substantially the same conditions as in Example 4 except that the above filter apparatus was employed. A good result was obtained with respect to the platelet recovery, which was 89%. However, the leukocyte removal efficiency of this filter apparatus was poor, because the sum of respective pore volumes of pores of the main porous element having a pore diameter of larger than 25 μm at which leakage of leukocytes occurred was as relatively large as 12%, based on the total pore volume, and the sum of respective pore surface areas of such pores was 5%, based on the total pore surface area. The leukocyte residual ratio was $10^{-2.5}$, showing a relatively poor leukocyte removal efficiency the pressure loss at the time of completion of the filtration was also as high as 90 mmHg. The surface area of the porous structure as required to treat platelets was 0.085 m² per $2 \times 10^{10}$ platelets.

COMPARATIVE EXAMPLE 9

The same gel-capturing material, MA-capturing material and preliminary porous element (first stage leukocyte-capturing material) as employed in Example 1 were packed into a container. Further, a spongy structure comprised of PU fibers having an average fiber diameter of 1.2 μm was disposed as a main porous element (second stage elukocyte-capturing material) under the most downstream end portion of the capturing materials so that the total thickness of the resultant porous structure became 3 mm (effective filtration cross-sectional area: 3.0 cm×3.0 cm). The above-mentioned individual capturing materials were hot-compressed in the same manner as in Example 1.

The main porous element disposed at the most downstream end portion of the porous structure had an average pore diameter of 2.5 μm, a total pore volume of 0.11 ml/ml of the main porous element and a total pore surface area of 0.49 m²/ml of the main porous element. In the main porous element, the sum of respective pore surface areas of pores having a pore diameter of 1 to 10 μm was 12%, based on the total pore surface area. The sum of respective pore volumes of pores having a pore diameter of 1 to 30 μm was 67%, based on the total pore volume, and the sum of respective pore surface areas of such pores was 14%, based on the total pore surface area. The sum of respective pore volumes of pores having a pore diameter of 1 to 25 μm was 66%, based on the total pore volume, and the sum of respective pore surface areas of such pores was 13%, based on the total pore surface area. The sum of respective pore volumes of pores having a pore diameter of larger than 30 μm was 3%, based on the total pore volume. The sum of respective pore surface areas of pores having a pore diameter of smaller than 1 μm was 85%, based on the total pore surface area. The sum of respective pore volumes of pores having a pore diameter of larger than 25 μm was 4%, based on the total pore volume, and the sum of respective pore surface areas of such pores was 2%, based on the total pore surface area. To the resultant leukocyte-removing filter apparatus was applied a coating of the same polymer prepared from HEMA and DM (DM content thereof: 3% by mole) as in Example 4. The above porous structure had a CWST value of 102 dyn/cm and a density of basic functional group of $9.6 \times 10^{-4}$ meq/m².

An experiment was conducted under substantially the same conditions as in Example 4 except that the above filter apparatus was employed. A good result was obtained with respect to the leukocyte residual ratio, which was $10^{-5.4}$. However, the platelet recovery was as poor as 51% and the pressure loss at the time of completion of the filtration was as high as not below 500 mmHg because the sum of respective pore surface areas of pores of the main porous element having a pore diameter of smaller than 1 μm at which a clogging with blood cells occurred was as large as 85%, based on the total pore surface area. The pore surface area of the porous structure as required to treat platelets was 0.12 m² per $2 \times 10^{10}$ platelets.

The results of the above Examples and Comparative Examples are shown in Table 1 and Table 2.

TABLE 1

| | | Example 1 | Comparative Example 1 | Example 2 | Comparative Example 2 | Comparative Example 3 | Example 3 | Comparative Example 4 | Comparative Example 5 |
|---|---|---|---|---|---|---|---|---|---|
| Average pore diameter (μm) | | 9.2 | 14.2 | 9.2 | 14.2 | 5.1 | 9.4 | 8.0 | 25.4 |
| Total pore volume (ml/ml of porous element) | | 0.85 | 0.72 | 0.85 | 0.72 | 0.37 | 0.81 | 0.41 | 0.55 |
| Total pore surface area (m²/ml of porous element) | | 0.95 | 0.56 | 0.95 | 0.56 | 0.55 | 0.90 | 0.59 | 0.60 |
| Pore diameter distribution (%) | | | | | | | | | |
| less than 1 μm | surface area | 28 | 42 | 28 | 42 | 53 | 26 | 44 | 33 |
| less than 2 μm | volume | 5 | 10 | 5 | 10 | 13 | 4 | 13 | 3 |
| | surface area | 39 | 57 | 39 | 57 | 64 | 38 | 57 | 46 |
| 2–10 μm | surface area | 53 | 29 | 53 | 29 | 33 | 55 | 35 | 41 |
| 1–30 μm | volume | 98 | 78 | 98 | 78 | 87 | 98 | 81 | 70 |
| | surface area | 71 | 56 | 71 | 56 | 46 | 73 | 54 | 58 |
| 2–30 μm | volume | 94 | 74 | 94 | 74 | 86 | 96 | 78 | 69 |
| | surface area | 60 | 34 | 60 | 34 | 35 | 61 | 41 | 46 |
| more than 30 μm | volume | 1 | 16 | 1 | 16 | 1 | 2 | 9 | 28 |
| Red cell recovery (%) | | 95 | 91 | 92 | 90 | 79 | 95 | 89 | 97 |
| Leukocyte residual ratio | | $10^{-4.2}$ | $10^{-2.2}$ | $10^{-5.2}$ | $10^{-3.2}$ | $10^{-4.8}$ | $10^{-5.1}$ | $10^{-3.4}$ | $10^{-1.4}$ |
| Pressure loss (mmHg) | | 103 | 118 | 132 | 148 | 500 or more | 108 | 205 | 51 |

TABLE 2

| | Example 4 | Comparative Example 6 | Comparative Example 7 | Example 5 | Comparative Example 8 | Comparative Example 9 |
|---|---|---|---|---|---|---|
| Average pore diameter (μm) | 9.2 | 10.6 | 16.2 | 7.4 | 8.1 | 2.5 |
| Total pore volume (ml/ml of porous element) | 0.83 | 0.79 | 0.86 | 0.73 | 0.58 | 0.11 |
| Total pore surface area (m²/ml of porous element) | 1.02 | 0.58 | 0.51 | 0.94 | 0.78 | 0.49 |
| Pore diameter distribution (%) | | | | | | |
| less than 1 μm   surface area | 27 | 42 | 40 | 34 | 47 | 85 |
| 1–10 μm           surface area | 63 | 44 | 39 | 60 | 41 | 12 |
| 1–25 μm           volume | 92 | 80 | 71 | 94 | 79 | 66 |
|                          surface area | 71 | 53 | 49 | 65 | 48 | 13 |
| 1–30 μm           volume | 95 | 84 | 77 | 96 | 81 | 67 |
|                          surface area | 72 | 54 | 51 | 66 | 50 | 14 |
| more than 25 μm   volume | 5 | 14 | 26 | 3 | 12 | 4 |
|                          surface area | 2 | 5 | 11 | 1 | 5 | 2 |
| more than 30 μm   volume | 2 | 8 | 20 | 1 | 10 | 3 |
| Platelet recovery (%) | 93 | 87 | 98 | 95 | 89 | 51 |
| Leukocyte residual ratio | $10^{-5.0}$ | $10^{-2.9}$ | $10^{-0.8}$ | $10^{-5.3}$ | $10^{-2.5}$ | $10^{-5.4}$ |
| Pressure loss (mmHg) | 48 | 85 | 26 | 62 | 90 | 500 or more |

EXAMPLE 6

A porous article comprised of PU laminates and having an average pore diameter of 30 μm at the upstream end portion thereof and an average pore diameter of 8 μm at the downstream end portion thereof was packed into a container having an effective filtration cross-sectional area of 43×43 mm. The total thickness of the resultant porous structure was 3 mm. The porous structure had a total pore volume of 0.80 ml/ml and a total pore surface area of 0.68 m²/ml at the downstream end portion thereof. In the porous structure, at the downstream end portion thereof, the sum of respective pore surface areas of pores having a pore diameter of 1 to 10 μm was 65%, based on the total pore surface area. The sum of respective pore volumes of pores having a pore diameter of 1 to 30 μm was 96%, based on the total volume, and the sum of respective pore surface areas of such pores was 74%, based on the total pore surface area. The sum of respective pore volumes of pores having a pore diameter of 1 to 25 μm was 93%, based on the total pore volume, and the sum of respective pore surface areas of such pores was 72%, based on the total pore surface area. The sum of respective pore volumes of pores having a pore diameter of larger than 25 μm was 4%, based on the total pore volume, and the sum of respective pore surface areas of such pores was 3%, based on the total pore surface area. The sum of respective pore surface areas of pores having a pore diameter of smaller than 1 μm was 25%, based on the total pore surface area. The sum of respective pore volumes of pores having a pore diameter of larger than 30 μm was 1%, based on the total pore volume. Through the resultant leukocyte-capturing filter apparatus, a 1% ethanol solution of a polymer prepared from HEMA and DM (DM content of the polymer: 3 mol %) was allowed to flow. Thereafter, nitrogen gas was passed, followed by drying under a vacuum of 1 mmHg or less at 40° C. for 24 hours. The porous structure had a density of basic functional group of $9.5 \times 10^{-4}$ meq/m² and a value of CWST of 102 dyn/cm.

460 ml of a platelet concentrate (30 ml of CPD solution had been added) was stored at room temperature while shaking for 2 days, and then filtered by means of a blood circuit in which the above leukocyte-capturing filter apparatus was incorporated.

An experiment was conducted under substantially the same conditions as in Example 4. Excellent results were obtained with respect to the leukocyte residual rate, the platelet recovery and the pressure loss at the time of completion of the filtration, which were $10^{-4.5}$, 92% and 26 mmHg, respectively. The surface area of the porous structure necessary to treat $2 \times 10^{10}$ of platelets was 0.049 m².

COMPARATIVE EXAMPLE 10

A porous article comprised of PU and having an average pore diameter of 8 μm was packed into a container having an effective filtration cross-sectional area of 43×43 mm, so that the total thickness of the resultant porous element became 3 mm. The porous element had a total pore volume of 0.73 ml/ml and a total pore surface area of 0.72 m²/ml at the downstream end portion thereof. In the porous element, the sum of respective pore surface area of pores having a pore diameter of 1 to 10 μm was 48%, based on the total pore surface area. The sum of respective pore volumes of pores having a pore diameter of 1 to 30 μm was 86%, based on the total volume, and the sum of respective pore surface areas of such pores was 53%, based on the total pore surface area. The sum of respective pore volumes of pores having a pore diameter of 1 to 25 μm was 81%, based on the total pore volume, and the sum of respective pore surface areas of such pores was 50%, based on the total pore surface area. The sum of respective pore volumes of pores having a pore diameter of larger than 25 μm was 10%, based on the total pore volume and the sum of respective pore surface areas of such pores was 8%, based on the total pore surface area. The sum of respective pore surface areas of pores having a pore diameter of smaller than 1 μm was 42%, based on the total pore surface area. The sum of respective pore volumes of pores having a pore diameter of larger than 30 μm was 5%, based on the total pore volume. To the resultant leukocyte-removing filter apparatus was applied a coating of the same polymer prepared from HEMA and DM (DM content thereof: 3% by mole) as in Example 6. The value of CWST and the density of basic functional group of the porous element were 102 dyn/cm and $9.7 \times 10^{-4}$ meq/m², respectively. Thereafter, a platelet product was filtered by means of the same blood circuit as employed in Example 6. A good result was obtained with respect to the platelet recovery, which was 83%. However, since the sum of respective pore volumes of pores of the porous element having a pore diameter of 1 to 25 μm which is effective for removal of leukocytes was as relatively small as 81%, based on the total pore volume, and the sum of respective pore surface areas of such pores was as relatively small as 50%, based on the total pore surface area, the leukocyte residual ratio was $10^{-3.1}$, showing a relatively poor leukocyte removal efficiency, and the pressure loss at the time of completion of the filtration was as high as 154 mmHg. The pore surface area of the porous element as required to treat platelets was 0.074 $m^2$ per $2\times10^{10}$ platelets.

COMPARATIVE EXAMPLE 11

A porous article comprised of PU laminates and having an average pore diameter of 315 μm at the upstream end portion thereof and an average pore diameter of 3 μm at the downstream end portion thereof was packed into a container having an effective filtration cross-sectional area of 43×43 mm, so that the total thickness of the resultant porous structure became 3 mm. The porous structure had a total pore volume of 0.24 ml/ml and a total pore surface area of 0.61 $m^2$/ml at the downstream end portion. In the porous structure, at the downstream end portion thereof, the sum of respective pore surface areas of pores having a pore diameter of 1 to 10 μm was 16%, based on the total pore surface area. The sum of respective pore volumes of pores having a pore diameter of 1 to 30 μm was 79%, based on the total volume, and the sum of respective pore surface areas of such pores was 18%, based on the total pore surface area. The sum of respective pore volumes of pores having a pore diameter of 1 to 25 μm was 79%, based on the total pore volume, and the sum of respective pore surface areas of such pores was 18%, based on the total pore surface area. The sum of respective pore volumes of pores having a diameter of larger than 25 μm was 0%, based on the total pore volume, and the sum of respective pore surface areas of such pores was 0%, based on the total pore surface area. The sum of respective pore surface areas of pores having a pore diameter of smaller than 1 μm was 82%, based on the total pore surface area. The sum of respective pore volumes of pores having a pore diameter of larger than 30 μm was 0%, based on the total pore volume. To the resultant leukocyte-removing filter apparatus was applied a coating of the same polymer prepared from HEMA and DM (DM content thereof: 3% by mole) as in Example 6. The value of CWST and the density of basic functional group of the porous structure were $9.5\times10^{-4}$ meq/$m^2$ and 102 dyn/cm, respectively. Thereafter, a platelet product was filtered by means of the same blood circuit as employed in Example 6. A good result was obtained with respect to the leukocyte residual ratio, which was $10^{-4.3}$. However, the platelet recovery of this filter apparatus was as poor as 40%, because the sum of respective pore surface areas of pores having a pore diameter of smaller than 1 μm at which a clogging with blood cells occurred was as high as 82%, based on the total pore surface area. Further, since the average pore diameter at the upstream end portion of the porous structure was equal to the average pore diameter at the downstream end portion thereof, the pressure loss at the time of completion of the filtration was as high as not below 500 mmHg. The surface area of the porous structure as required to treat platelets was 0.030 $m^2$ per $2\times10^{10}$ platelets.

COMPARATIVE EXAMPLE 12

Porous articles comprised of polyurethane were laminated upon one another to thereby obtain a porous structure so that the upstream end portion of the porous structure had an average pore diameter of 80 μm and the downstream end portion of the porous structure had an average pore diameter of 25 μm. The porous structure was packed into a container having an effective filtration cross-sectional area of 43×43 mm so that the thickness of the packed porous structure became 3 mm, to thereby obtain a filter apparatus. The downstream end portion of the porous structure had a total pore volume of 0.91 ml/ml of the main porous element and a total pore surface area of 0.22 $m^2$/ml of the main porous element. In the main porous element, the sum of respective pore surface areas of pores having a pore diameter of 1 to 10 μm was 35%, based on the total pore surface area. The sum of respective pore volumes of pores having a pore diameter of 1 to 30 μm was 56%, based on the total pore volume and the sum of respective pore surface areas of the pores was 45%, based on the total pore surface area. The sum of respective pore volumes of pores having a pore diameter of 1 to 25 μm was 50%, based on the total pore volume and the sum of respective pore surface areas of the pores was 41%, based on the total pore surface area. The sum of respective pore volumes of pores having a pore diameter of larger than 25 μm was 48%, based on the total pore volume and the sum of respective pore surface areas of the pores was 28%, based on the total pore surface area. The sum of respective pore surface areas of pores having a pore diameter of smaller than 1 μm was 31%, based on the total pore surface area and the sum of respective pore volumes of pores having a pore diameter of larger than 30 μm was 42%, based on the total pore volume. The porous structure in the thus obtained filter apparatus for removing leukocytes was subjected to coating with the same polymer as employed in Example 6 so that the main porous element had a CWST value of 102 dyn/cm and had a basic functional group at a density of $9.2\times10^{-4}$ meq/$m^2$. Then, a platelet product was subjected to leukocyte removal treatment by means of the above-obtained filter apparatus and, connected thereto, the same blood circuit as employed in Example 6. As a result of the filtration, the platelet recovery was 93% and the pressure loss at the time of completion of the filtration was 18 mmHg, which were good. However, since in the main porous element, the sum of respective pore volumes of pores having a pore diameter of more than 25 μm, which pores are likely to cause a leakage of lymphocytes was as high as 48%, based on the total pore volume and the sum of respective pore surface areas of the pores was as high as 28%, based on the total surface area, the leukocyte residual ratio was as high as $10^{-1.3}$, indicating a low leukocyte removal efficiency. The porous structure had a pore surface area of 0.022 $m^2$ per $2\times10^{10}$ platelets contained in the platelet product subjected to the filtration.

COMPARATIVE EXAMPLE 13

Porous articles comprised of polyurethane were laminated upon one another to thereby obtain a porous structure so that the upstream end portion of the porous structure had an average pore diameter of 25 μm and the downstream end portion of the porous structure had an average pore diameter of 5 μm. The porous structure was packed into a container having an effective filtration cross-sectional area of 43×43 mm so that the thickness of the packed porous structure became 3 mm, to thereby obtain a filter apparatus. The downstream end portion of the porous structure had a total pore volume of 0.82 ml/ml of the main porous element and a total pore surface area of 1.04 $m^2$/ml of the main porous element. In the main porous element, the sum of respective pore surface areas of pores having a pore diameter of 1 to 10

μm was 52%, based on the total pore surface area. The sum of respective pore volumes of pores having a pore diameter of 1 to 30 gm was 88%, based on the total pore volume and the sum of respective pore surface areas of the pores was 58%, based on the total pore surface area. The sum of respective pore volumes of pores having a pore diameter of 1 to 25 μm was 84%, based on the total pore volume and the sum of respective pore surface areas of the pores was 56%, based on the total pore surface area. The sum of respective pore volumes of pores having a pore diameter of larger than 25 μm was 5%, based on the total pore volume and the sum of respective pore surface areas of the pores was 2%, based on the total pore surface area. The sum of respective pore surface areas of pores having a pore diameter of smaller than 1 μm was 42%, based on the total pore surface area, and the sum of respective pore volumes of pores having a pore diameter of larger than 30 μm was 1%, based on the total pore volume. The porous structure in the thus obtained filter apparatus for removing leukocytes was subjected to coating with the same polymer as employed in Example 6 so that the main porous element had a CWST Value of 102 dyn/cm and had a basic functional group at a density of $9.2 \times 10^{-4}$ meq/m². Then, a platelet product was subjected to leukocyte removal treatment by means of the thus obtained filter apparatus and, connected thereto, the same blood circuit as employed in Example 6. As a result of the filtration, the leukocyte residual ratio was $10^{-3.7}$, indicating a slightly low leukocyte removal efficiency. Further, because the porous structure had a pore surface area as large as 0.12 m² per $2 \times 10^{10}$ platelets contained in the platelet product subjected to the filtration, the platelet recovery was as low as 71% and the pressure loss at the time of completion of the filtration was as high as 237 mmHg.

EXAMPLE 7

Porous articles comprised of cellulose were laminated upon one another to thereby obtain a porous structure so that the upstream end portion of the porous structure had an average pore diameter of 50 μm and the downstream end portion of the porous structure had an average pore diameter of 12 μm. The porous structure was packed into a container having an effective filtration cross-sectional area of 67×67 mm so that the thickness of the packed porous structure became 5 mm, to thereby obtain a filter apparatus. The downstream end portion of the porous structure had a total pore volume of 0.84 ml/ml of the main porous element and a total pore surface area of 0.81 m²/ml of the main porous element. In the main porous element, the sum of respective pore surface areas of pores having a pore diameter of 2 to 10 μm was 52%, based on the total pore surface area. The sum of respective pore volumes of pores having a pore diameter of 1 to 30 μm was 98%, based on the total pore volume and the sum of respective pore surface areas of the pores was 70%, based on the total pore surface area. The sum of respective pore volumes of pores having a pore diameter of 2 to 30 μm was 96%, based on the total pore volume and the sum of respective pore surface areas of the pores was 62%, based on the total pore surface area. The sum of respective pore volumes of pores having a pore diameter of smaller than 2 μm was 3%, based on the total pore volume and the sum of respective pore surface areas of the pores was 36%, based on the total pore surface area. The sum of respective pore surface areas of pores having a pore diameter of smaller than 1 μm was 26%, based on the total pore surface area, and the sum of respective pore volumes of pores having a pore diameter of greater than 30 μm was 1%, based on the total pore volume. A 0.5% solution of a polymer comprised of HEMA and DM (the DM content of the polymer: 30% by mole) was passed through the thus obtained filter apparatus for selectively removing leukocytes and the resultant coated porous structure was subjected to drying in the same manner as in Example 2. The CWST value of the main porous element became 82 dyn/cm and the density of the basic functional group in the surface portion of the main porous element was $4.5 \times 10^{-3}$ meq/m².

An experiment was conducted under substantially the same conditions as in Example 2 except that the above-obtained filter apparatus was used. Good results were obtained. That is, the leukocyte residual ratio was $10^{-4.8}$, the red cell recovery was 93% and the pressure loss at the time of completion of the filtration was 136 mmHg.

COMPARATIVE EXAMPLE 14

A porous article comprised of cellulose and having a uniform average pore diameter of 12 μm was packed into a container having an effective filtration cross-sectional area of 67×67 mm so that the thickness of the resultant packed porous structure became 5 mm, to thereby obtain a filter apparatus. The downstream end portion of the porous structure had a total pore volume of 0.38 ml/ml of the main porous element and a total pore surface area of 0.45 m²/ml of the main porous element. In the main porous element, the sum of respective pore surface areas of pores having a pore diameter of 2 to 10 μm was 34%, based on the total pore surface area. The sum of respective pore volumes of pores having a pore diameter of 1 to 30 μm was 74%, based on the total pore volume and the sum of respective pore surface areas of the pores was 55%, based on the total pore surface area. The sum of respective pore volumes of pores having a pore diameter of 2 to 30 μm was 73%, based on the total pore volume and the sum of respective pore surface areas of the pores was 48%, based on the total pore surface area. The sum of respective pore volumes of pores having a pore diameter of smaller than 2 μm was 7%, based on the total pore volume and the sum of respective pore surface areas of the pores was 49%, based on the total pore surface area. The sum of respective pore surface areas of pores having a pore diameter of smaller than 1 μm was 42%, based on the total pore surface area, and the sum of respective pore volumes of pores having a pore diameter of greater than 30 μm was 20%, based on the total pore volume. The porous structure in the thus obtained filter apparatus for selectively removing leukocytes was subjected to coating with the same polymer as employed in Example 7 so that the CWST value and the density of the basic functional group became 84 dyn/cm and $4.5 \times 10^{-3}$ meq/m², respectively. Then, a red cell product was subjected to leukocyte removal treatment by means of the thus-obtained filter apparatus and, connected thereto, the same blood circuit as employed in Example 7. As a result, the red cell recovery was 85% which was slightly low. In addition, since in the main porous element, the sum of respective pore volumes of pores having a pore diameter of more than 30 μm which pores are likely to cause a leakage of lymphocytes was as large as 20%, based on the total pore volume, the leukocyte residual ratio was $10^{-3.7}$, indicating a slightly low leukocyte removal efficiency. Further, since the upstream end portion and downstream end portion of the porous structure were the same in the average pore diameter, a clogging occurred in the upstream end portion of the porous structure and the pressure loss at the time of completion of the filtration was as high as 348 mmHg.

COMPARATIVE EXAMPLE 15

Porous articles comprised of cellulose were laminated upon one another to thereby obtain a porous structure so that the upstream end portion of the porous structure had an average pore diameter of 310 μm and the downstream end portion of the porous structure had an average pore diameter of 3 μm. The porous structure was packed into a container having an effective filtration cross-sectional area of 67×67 mm so that the thickness of the packed porous structure became 5 mm, to thereby obtain a filter apparatus. The downstream end portion of the porous structure had a total pore volume of 0.75 ml/ml of the main porous element and a total pore surface area of 1.20 $m^2$/ml of the main porous element. In the main porous element, the sum of respective pore surface areas of pores having a pore diameter of 2 to 10 μm was 32%, based on the total pore surface area. The sum of respective pore volumes of pores having a pore diameter of 1 to 30 μm was 88%, based on the total pore volume and the sum of respective pore surface areas of the pores was 42%, based on the total pore surface area. The sum of respective pore volumes of pores having a pore diameter of 2 to 30 μm was 86%, based on the total pore volume and the sum of respective pore surface areas of the pores was 34%, based on the total pore surface area. The sum of respective pore volumes of pores having a pore diameter of smaller than 2 μm was 12%, based on the total pore volume and the sum of respective pore surface areas of the pores was 64%, based on the total pore surface area. The sum of respective pore surface areas of pores having a pore diameter of smaller than 1 μm was 57%, based on the total pore surface area, and the sum of respective pore volumes of pores having a pore diameter of greater than 30 μm was 2%, based on the total pore volume. The porous structure in the thus obtained filter apparatus for removing leukocytes was subjected to coating with the same polymer as employed in Example 7 so that the CWST value and the density of the basic functional group became 82 dyn/cm and $4.0 \times 10^{-3}$ meq/$m^2$, respectively. Then, a red cell product was subjected to leukocyte removal treatment by means of the thus obtained filter apparatus and, connected thereto, the same blood circuit as employed in Example 7. As a result, the leukocyte residual ratio was $10^{-4.5}$, which was good. However because, in the main porous element, the sum of respective pore surface areas of pores having a pore diameter of smaller than 2 μm, which pores are unlikely to allow passage of blood cells was as large as 64%, based on the total pore surface area, and because the average pore diameter ratio of the upstream end portion to the downstream end portion of the porous structure was as large as 103, a clogging occurred in the downstream end portion of the porous structure and the red cell recovery was as low as 79% and the pressure loss at the time of completion of the filtration was as high as 500 mmHg or more.

COMPARATIVE EXAMPLE 16

Porous articles comprised of cellulose were laminated upon one another to thereby obtain a porous structure so that the upstream end portion of the porous structure had an average pore diameter of 105 μm and the downstream end portion of the porous structure had an average pore diameter of 30 μm. The porous structure was packed into a container having an effective filtration cross-sectional area of 67×67 mm so that the thickness of the packed porous structure became 5 mm, to thereby obtain a filter apparatus. The downstream end portion of the porous structure had a total pore volume of 0.69 ml/ml of the main porous element and a total pore surface area of 0.20 $m^2$/ml of the main porous element. In the main porous element, the sum of respective pore surface areas of pores having a pore diameter of 2 to 10 μm was 25%, based on the total pore surface area. The sum of respective pore volumes of pores having a pore diameter of 1 to 30 μm was 66%, based on the total pore volume and the sum of respective pore surface areas of the pores was 55%, based on the total pore surface area. The sum of respective pore volumes of pores having a pore diameter of 2 to 30 μm was 65%, based on the total pore volume and the sum of respective pore surface areas of the pores was 40%, based on the total pore surface area. The sum of respective pore volumes of pores having a pore diameter of smaller than 2 μm was 1%, based on the total pore volume and the sum of respective pore surface areas of the pores was 46%, based on the total pore surface area. The sum of respective pore surface areas of pores having a pore diameter of smaller than 1 μm was 31%, based on the total pore surface area and the sum of respective pore volumes of pores having a pore diameter of greater than 30 μm was 34%, based on the total pore volume. The porous structure in the thus obtained filter apparatus for removing leukocytes was subjected to coating with the same polymer as employed in Example 7 so that the CWST value and the density of the basic functional group became 82 dyn/cm and $4.8 \times 10^{-3}$ meq/$m^2$, respectively. Then a red cell product was subjected to leukocyte removal treatment by means of the thus obtained filter apparatus and, connected thereto, the same blood circuit as employed in Example 7. As a result, the red cell recovery was 95% and the pressure loss at the time of completion of the filtration was 46 mmHg, which were good. However, since in the main porous element, the sum of respective pore volumes of pores having a pore diameter of more than 30 μm, which pores are likely to cause a leakage of leukocytes was as large as 34%, based on the total pore volume, the leukocyte residual ratio was $10^{-1.5}$, indicating a low leukocyte removal efficiency.

COMPARATIVE EXAMPLE 17

Porous articles comprised of cellulose were laminated upon one another to thereby obtain a porous structure so that the upstream end portion of the porous structure had an average pore diameter of 30 μm and the downstream end portion of the porous structure had an average pore diameter of 5 μm. The porous structure was packed into a container having an effective filtration cross-sectional area of 67×67 mm so that the thickness of the packed porous structure became 5 mm, to thereby obtain a filter apparatus. The downstream end portion of the porous structure had a total pore volume of 0.41 ml/ml of the main porous element and a total pore surface area of 0.52 $m^2$/ml of the main porous element. In the main porous element, the sum of respective pore surface areas of pores having a pore diameter of 2 to 10 μm was 41%, based on the total pore surface area. The sum of respective pore volumes of pores having a pore diameter of 1 to 30 μm was 84%, based on the total pore volume and the sum of respective pore surface areas of the pores was 53%, based on the total pore surface area. The sum of respective pore volumes of pores having a pore diameter of 2 to 30 μm was 83%, based on the total pore volume and the sum of respective pore surface areas of the pores was 46%, based on the total pore surface area. The sum of respective pore volumes of pores having a pore diameter of smaller than 2 μm was 16%, based on the total pore volume and the sum of respective pore surface areas of the pores was 53%, based on the total pore surface area. The sum of respective pore surface areas of pores having a pore diameter of smaller than 1 μm was 46%, based on the total pore surface area, and the sum of respective pore volumes of pores having a pore diameter of greater than 30 μm was 1%, based on the total pore volume. The porous structure in the thus obtained filter apparatus for removing leukocytes was subjected to coating with the same polymer as employed in Example 7 so that the CWST value and the density of the basic functional group became 84 dyn/cm and $4.3 \times 10^{-3}$ meq/m$^2$, respectively. Then, a red cell product was subjected to leukocyte removal treatment by means of the thus obtained filter apparatus and, connected thereto, the same blood circuit as employed in Example 7. As a result, the leukocyte residual ratio was $10^{-3.5}$ and the red cell recovery was 86%, which were slightly poor. The pressure loss at the time of completion of the filtration was as high as 269 mmHg.

The results obtained in Examples 6 and 7 and Comparative Examples 10 to 17 are shown in Tables 3 and 4.

Industrial Applicability

The porous element of the filter material according to the present invention has a feature that the ratio of the sum of respective pore volumes of pores having a pore diameter of 1 to 30 μm is high. The filter material exhibits an excellent leukocyte removal efficiency without suffering from a pressure loss increase as compared to the conventional filter materials. In addition, a filter apparatus packed with this filter material can be rendered in compact. When this filter apparatus is used for treatment of a leukocyte-containing suspension, not only is occurrence of side effects of a blood component transfusion decreased, but also leukocytes can be efficiently removed without removal of effective

TABLE 3

| | | Example 6 | Comparative Example 10 | Comparative Example 11 | Comparative Example 12 | Comparative Example 13 |
|---|---|---|---|---|---|---|
| Average pore diameter (μm) | Upstream end portion | 30 | 8 | 315 | 80 | 25 |
| | Downstream end portion | 8 | 8 | 3 | 25 | 5 |
| Average pore diameter ratio: upstream end portion/downstream end portion | | 3.8 | 1.0 | 105 | 3.2 | 5.0 |
| Downstream end portion | Total pore volume (ml/ml) | 0.80 | 0.73 | 0.24 | 0.91 | 0.82 |
| | Total pore surface area (m$^2$/ml) | 0.68 | 0.72 | 0.61 | 0.22 | 1.04 |
| Pore diameter distribution of the downstream end portion (%) | less than 1 μm surface area | 25 | 42 | 82 | 31 | 42 |
| | 1–10 μm surface area | 65 | 48 | 16 | 35 | 52 |
| | 1–30 μm volume | 96 | 86 | 79 | 56 | 88 |
| | surface area | 74 | 53 | 18 | 45 | 58 |
| | 1–25 μm volume | 93 | 81 | 79 | 50 | 84 |
| | surface area | 72 | 50 | 18 | 41 | 56 |
| | more than 25 μm volume | 4 | 10 | 0 | 48 | 5 |
| | surface area | 3 | 8 | 0 | 28 | 2 |
| | more than 30 μm volume | 1 | 5 | — | 42 | 1 |
| Platelet recovery (%) | | 92 | 83 | 40 | 93 | 71 |
| Leukocyte residual ratio | | $10^{-4.5}$ | $10^{-3.1}$ | $10^{-4.3}$ | $10^{-1.3}$ | $10^{-3.7}$ |
| Pressure loss (mmHg) | | 26 | 154 | 500 or more | 18 | 237 |

TABLE 4

| | | Example 7 | Comparative Example 14 | Comparative Example 15 | Comparative Example 16 | Comparative Example 17 |
|---|---|---|---|---|---|---|
| Average pore diameter (μm) | Upstream end portion | 50 | 12 | 310 | 105 | 30 |
| | Downstream end portion | 12 | 12 | 3 | 30 | 5 |
| Average pore diameter ratio: upstream end portion/downstream end portion | | 4.2 | 1.0 | 103 | 3.5 | 6.0 |
| Downstream end portion | Total pore volume (ml/ml) | 0.84 | 0.38 | 0.75 | 0.69 | 0.41 |
| | Total pore surface area (m$^2$/ml) | 0.81 | 0.45 | 1.20 | 0.20 | 0.52 |
| Pore diameter distribution of the downstream end portion (%) | less than 1 μm surface area | 26 | 42 | 57 | 31 | 46 |
| | less than 2 μm volume | 3 | 7 | 12 | 1 | 16 |
| | surface area | 36 | 49 | 64 | 46 | 53 |
| | 2–10 μm surface area | 52 | 34 | 32 | 25 | 41 |
| | 1–30 μm volume | 98 | 74 | 88 | 66 | 84 |
| | surface area | 70 | 55 | 42 | 55 | 53 |
| | 2–30 μm volume | 96 | 73 | 86 | 65 | 83 |
| | surface area | 62 | 48 | 34 | 40 | 46 |
| | more than volume | 1 | 20 | 2 | 34 | 1 |
| Red cell recovery (%) | | 93 | 85 | 79 | 95 | 86 |
| Leukocyte residual ratio | | $10^{-4.8}$ | $10^{-3.7}$ | $10^{-4.5}$ | $10^{-1.5}$ | $10^{-3.5}$ |
| Pressure loss (mmHg) | | 136 | 348 | 500 or more | 46 | 269 |

We claim:

1. A filter apparatus for selectively removing leukocytes from a leukocyte-containing suspension, which comprises a container having an inlet for a leukocyte-containing suspension and an outlet for a filtrate, and a porous structure packed in said container, said porous structure comprising a main porous element having an average pore diameter of 1 to 25 μm and a total pore volume of 0.40 to 0.95 ml/ml of the main porous element, wherein the sum of respective pore volumes of pores of said main porous element which have a pore diameter of 1 to 30 μm is 90% or more, based on said total pore volume, and at least one preliminary porous element disposed upstream of said main porous element with respect to a flow direction in which a leukocyte-containing suspension to be treated for removal of leukocytes is adapted to be flowed, said preliminary porous element having an average pore diameter which is larger than the average pore diameter of said main porous element so that said porous structure has an average pore diameter of 1 to 300 μm, said porous structure having an average pore diameter gradient such that the average pore diameter is substantially continuously or stepwise decreased in said flow direction from an upstream end portion to a downstream end portion of the porous structure, wherein said upstream end portion and said downstream end portion each have a thickness of 0.5 mm or less, as measured in a thicknesswise direction from the upstream end surface and from the downstream end surface of said porous structure, respectively, and wherein said upstream end portion of said porous structure has an average pore diameter of 10 to 300 μm and said downstream end portion of said porous structure has an average pore diameter of 1 to 25 μm, with the proviso that the average pore diameter of the upstream end portion of said porous structure is 2 to 100 times that of the downstream end portion of said porous structure, wherein said preliminary porous element is capable of capturing at least 60% of all leukocytes contained in said leukocyte-containing suspension.

2. The filter apparatus according to claim 1, wherein said main porous element has a total pore surface area of 0.50 to 5.70 m²/ml of the main porous element, and wherein the sum of respective pore surface areas of pores of said main porous element which have a pore diameter of 1 to 30 μm is 60% or more, based on said total pore surface area.

3. The filter apparatus according to claim 2, wherein in the sum of respective pore surface areas of pores of said main porous element which have a pore diameter of 1 to 10 μm is 50% or more, based on said total pore surface area.

4. The filter apparatus according to claim 1, wherein said containing suspension is a leukocyte-containing red cell product, and wherein said main porous element has an average pore diameter of 3 to 25 μm, with the proviso that the sum of respective pore volumes of pores of said main porous element which have a pore diameter of 2 to 30 μm is 85% or more, based on said total pore volume and wherein the sum of respective pore surface areas of pores of said main porous element which have a pore diameter of 2 to 30 μm is 50% or more based on said total pore surface area, and the sum of respective pore surface areas of pores of said main porous element which have a pore diameter of 2 to 10 μm is 35% or more, based on said total pore surface area.

5. The filter apparatus according to claim 4, wherein said porous structure further comprises at least one preliminary porous element disposed upstream of said main porous element with respect to a flow direction in which a leukocyte-containing red cell product to be treated for removal of leukocytes is adapted to be flowed, said preliminary porous element having an average pore diameter which is larger than the average pore diameter of said main porous element so that said porous structure has an average pore diameter of 3 to 300 μm, and wherein said porous structure has an average pore diameter gradient such that the average pore diameter is substantially continuously or stepwise decreased in said flow direction from an upstream end portion to a downstream end portion of the porous structure, said upstream end portion and said downstream end portion each having a thickness of 0.5 mm or less, as measured in a thicknesswise direction from the upstream end surface and from the downstream end surface of said porous structure, respectively.

6. The filter apparatus according to claim 5, wherein said upstream end portion of said porous structure has an average pore diameter of 15 to 300 μm and said downstream end portion of said porous structure has an average pore diameter of 3 to 25 μm, with the proviso that said average pore diameter of said upstream end portion is 3 to 100 times that of said downstream end portion of said porous structure.

7. The filter apparatus according to claim 1, wherein said leukocyte-containing suspension is a leukocyte-containing platelet product, and wherein said main porous element has an average pore diameter of 1 to 15 μm with the proviso that the sum of respective pore volumes of pores of said main porous element which have a pore diameter of 1 to 25 μm is 85% or more, based on said total pore volume, wherein the sum of respective pore surface areas of pores of said main porous element which have a pore diameter of 1 to 25 μm is 58% or more, based on said total pore surface area, and wherein the sum of respective pore surface areas of pores of said main porous element which have a pore diameter of 1 to 10 μm is 55% or more, based on said total pore surface area.

8. The filter apparatus according to claim 7, wherein said porous structure further comprises at least one preliminary porous element disposed upstream of said main porous element with respect to a flow direction in which a leukocyte-containing platelet product to be treated for removal of leukocytes is adapted to be flowed, said preliminary porous element having an average pore diameter which is larger than the average pore diameter of said main porous element so that said porous structure has an average pore diameter of 1 to 200 μm, and wherein said porous structure has an average pore diameter gradient such that the average pore diameter is substantially continuously or stepwise decreased in said flow direction from an upstream end portion to a downstream end portion of said porous structure, said upstream end portion and said downstream end portion each having a thickness of 0.5 mm or less, as measured in a thicknesswise direction from the upstream end surface and from the downstream end surface of said porous structure, respectively.

9. The filter apparatus according to claim 8, wherein said upstream end portion of said porous structure has an average pore diameter of 10 to 200 μm and said downstream end portion of said porous structure has an average pore diameter of 1 to 15 μm, with the proviso that said average pore diameter of said upstream end portion of said porous structure is 2 to 60 times that of said downstream end portion of said porous structure.

10. The filter apparatus according to claim 7, wherein said porous structure has a pore surface area of 0.01 to 0.08 m² per $2 \times 10^{10}$ platelets contained in said platelet product.

* * * * *